(12) United States Patent
Nishiyama et al.

(10) Patent No.: US 11,484,235 B2
(45) Date of Patent: Nov. 1, 2022

(54) METHOD OF DETERMINING A STRESS TIME PERIOD OF A PERSON

(71) Applicant: Panasonic Intellectual Property Management Co., Ltd., Osaka (JP)

(72) Inventors: Yukari Nishiyama, Tokyo (JP); Masahiko Tsukuda, Osaka (JP); Yasuaki Okumura, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 595 days.

(21) Appl. No.: 16/583,317

(22) Filed: Sep. 26, 2019

(65) Prior Publication Data

US 2020/0015731 A1    Jan. 16, 2020

Related U.S. Application Data

(63) Continuation of application No. PCT/JP2018/021459, filed on Jun. 5, 2018.

(30) Foreign Application Priority Data

Jul. 7, 2017  (JP) .............................. JP2017-133371

(51) Int. Cl.
*A61B 5/16*  (2006.01)
*A61B 5/00*  (2006.01)
*G01N 33/497*  (2006.01)

(52) U.S. Cl.
CPC ............ *A61B 5/165* (2013.01); *A61B 5/0022* (2013.01); *A61B 5/6801* (2013.01); *A61B 5/742* (2013.01);
(Continued)

(58) Field of Classification Search
CPC ..... A61B 5/165; A61B 5/0022; A61B 5/6801; A61B 5/742; G01N 33/497; G01N 2033/4975
See application file for complete search history.

(56) References Cited

U.S. PATENT DOCUMENTS

| 2008/0146892 A1 | 6/2008 | LeBoeuf et al. |
| 2016/0058376 A1 | 3/2016 | Baek et al. |
| 2016/0270704 A1 | 9/2016 | DeTurk |

FOREIGN PATENT DOCUMENTS

| AU | 2003263969 | * | 6/2004 | ............. A61B 5/002 |
| DE | 10339015 | * | 3/2005 | ........... A61B 5/4283 |

(Continued)

OTHER PUBLICATIONS

International Search Report of PCT application No. PCT/JP2018/021459 dated Sep. 4, 2018.
(Continued)

*Primary Examiner* — Hongmin Fan
(74) *Attorney, Agent, or Firm* — Greenblum & Bernstein, P.L.C.

(57) ABSTRACT

To objectively grasp a stress state of a user and to prevent a mental disorder of the user, the following steps are performed: acquiring, via a network, biogas information at multiple timings and time information corresponding to each of the multiple timings, wherein the biogas information represents a concentration of tetradecane of a user acquired by a sensor that detects tetradecane discharged from a skin surface of the user; obtaining reference information representing an upper limit of a normal range of the concentration of tetradecane per unit period of time, using a memory storing the reference information representing the upper limit of the normal range; determining a stress time period during which a concentration of the tetradecane of the user is more than the upper limit of the normal range, based on
(Continued)

the acquired biological gas information; and outputting time period information indicating the determined stress time period to an information terminal of the user, to display the stress time period indicated by the time period information on a display of the information terminal.

10 Claims, 19 Drawing Sheets

(52) U.S. Cl.
CPC ... *G01N 33/497* (2013.01); *G01N 2033/4975* (2013.01)

(56) References Cited

FOREIGN PATENT DOCUMENTS

| JP | 2005-046305 | | 2/2005 |
|----|----|----|----|
| JP | 2010022554 | * | 2/2010 |

OTHER PUBLICATIONS

Japanese Cabinet Office, "White Paper on National Life (2008)", Chapter 1, Section 3, "2. Stressful Society and Modern pathology", Dec. 26, 2008 (Whole Sentence Translation).
General Conference (2013), Special Lectures, "Grasping Metal Problems of Pregnant Woman and Child Care", Keiko Yoshida, Child Health in Okinawa, vol. 41 (2014), Mar. 2014, pp. 3-8 (Whole Sentence Translation).
English Translation of Chinese Search Report dated Dec. 6, 2021 for the related Chinese Patent Application No. 201880028255.5.
English Translation of Chinese Search Report dated Apr. 26, 2021 for the related Chinese Patent Application No. 201880028255.5.

* cited by examiner

TETRADECANE

DATA BASE (NIST)

FIG. 4

TETRADECANE

|  | DURING STRESS TASK | AFTER STRESS TASK | DURING RELAX TASK | AFTER RELAX TASK |
|---|---|---|---|---|
| No.1 | 88526 | 132224 | 146496 | 194037 |
| No.2 | 107376 | 90044 | 99887 | 104024 |
| No.3 | 119068 | 94867 | 89204 | 111997 |
| No.4 | 106216 | 136208 | 122366 | 136353 |
| No.5 | 93808 | 133026 | 84186 | 60901 |
| No.6 | 406939 | 202015 | 58420 | 60312 |
| No.7 | 103773 | 99484 | 74726 | 86419 |
| No.8 | 135855 | 112520 | 102163 | 134714 |
| No.9 | 121896 | 91538 | 74160 | 68644 |
| No.10 | 117242 | 133835 | 84237 | 112753 |
| No.11 | 105197 | 47393 | 63102 | 46046 |
| No.12 | 95643 | 59687 | 68807 | 74790 |
| No.13 | 121612 | 103673 | 77810 | 70874 |
| No.14 | 81648 | 91775 | 85150 | 103617 |
| No.15 | 103282 | 82118 | 59920 | 115992 |
| No.16 | 80288 | 40137 | 61801 | 41580 |
| No.17 | 79846 | 56837 | 50798 | 52392 |
| No.18 | 140183 | 86783 | 49058 | 55949 |
| No.19 | 67861 | 56871 | 44480 | 75356 |
| No.20 | 98247 | 105094 | 133376 | 60106 |
| AVERAGE | 118725 | 97806 | 81507 | 88343 |

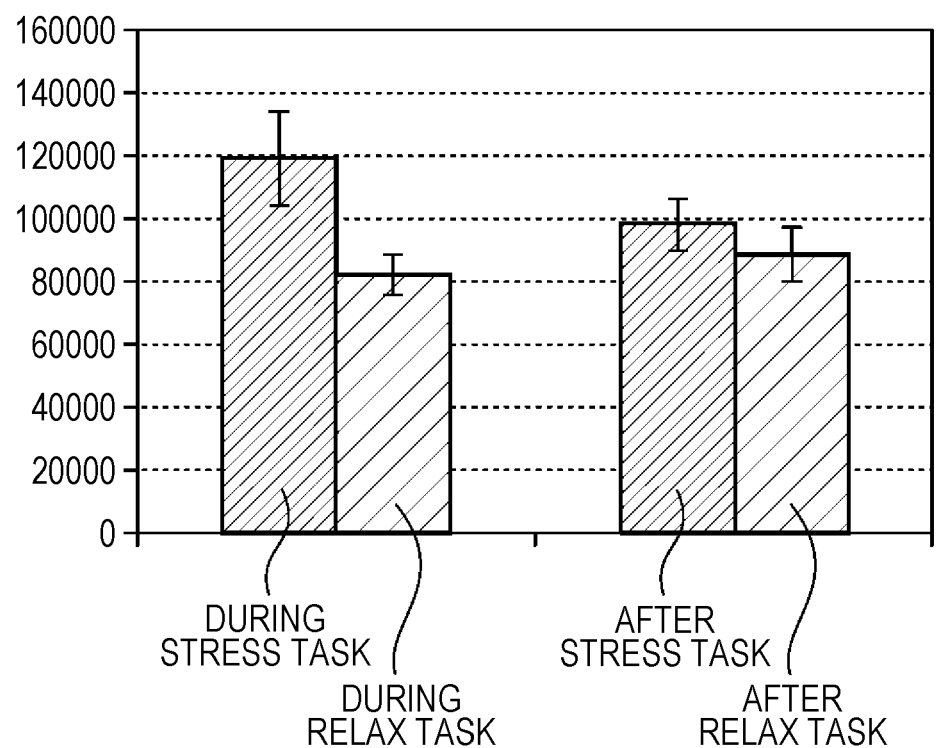

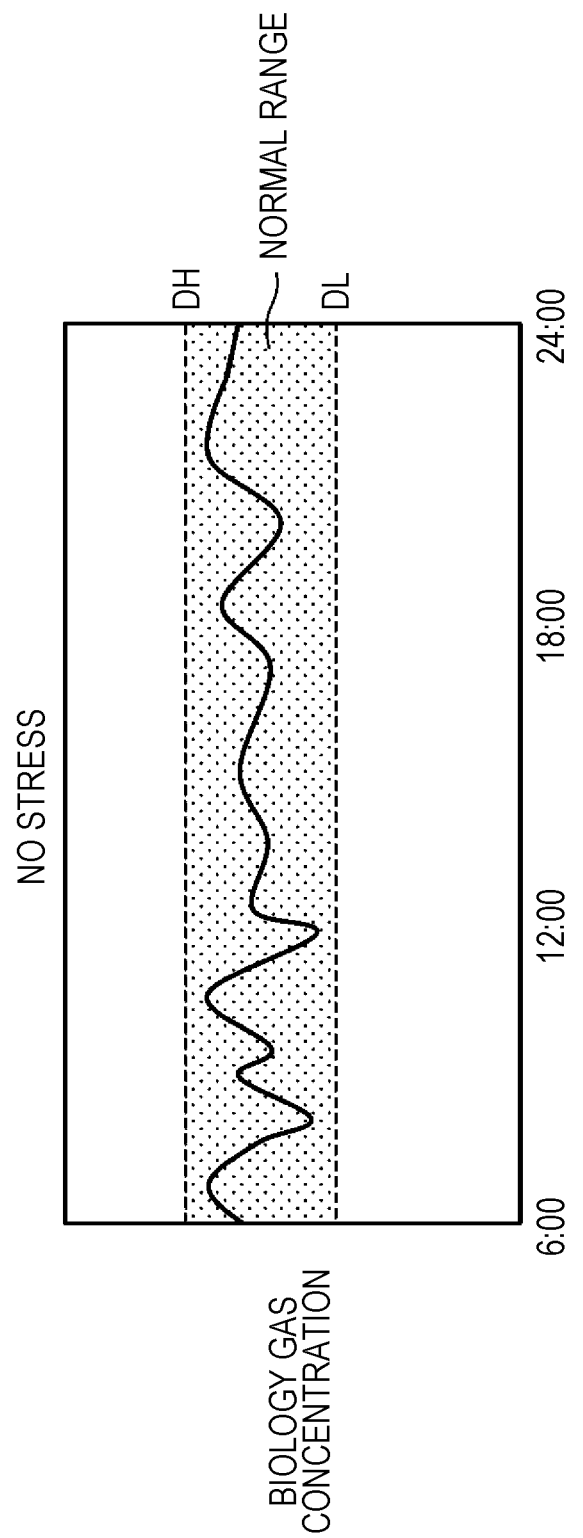

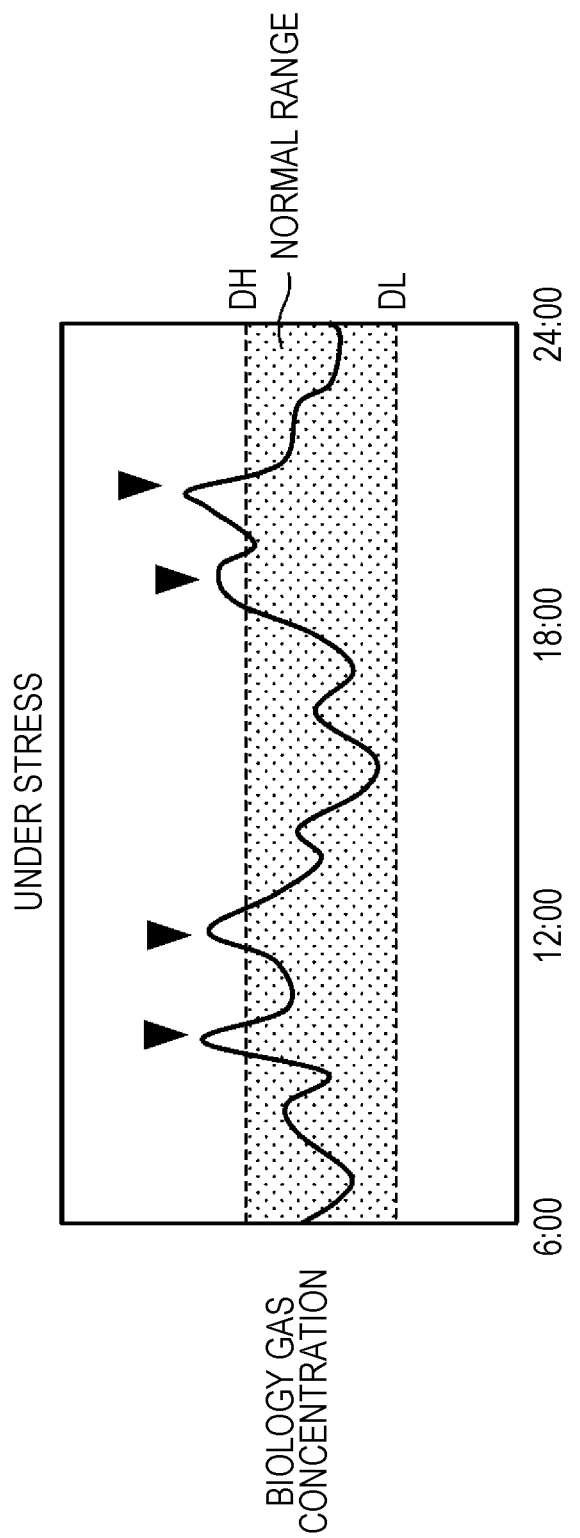

FIG. 19
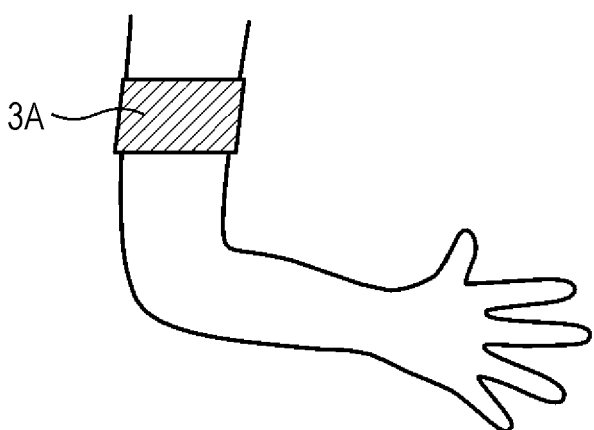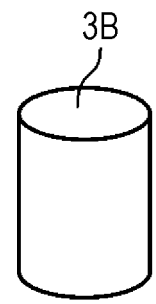

METHOD OF DETERMINING A STRESS TIME PERIOD OF A PERSON

BACKGROUND

Technical Field

The present disclosure relates to an information provision method and the like.

Background Art

PTL 1 discloses a wristwatch-type conversation assistance device to which a perspiration sensor, a pulse sensor, and a blood flow sensor are attached.

The wristwatch-type conversation assistance device measures emotion of a user wearing the wristwatch-type conversation assistance device by using the perspiration sensor, the pulse sensor, and the blood flow sensor, and displays, with characters and the like, a result of information processing performed based on a result of the measurements by the sensors. For example, as the result of the measurements using the perspiration sensor, the pulse sensor, and the blood flow sensor, if the user is slightly angry, the wristwatch-type conversation assistance device displays "Slightly angry". If the user is slightly angry, the wristwatch-type conversation assistance device additionally displays a message saying, for example, "Talk calmly".

Further, PTL 1 discloses a system that displays a measurement result by a perspiration sensor and a blood flow sensor attached inside a shoe, on a wristwatch-type acquisition and display device with characters and the like. In a similar manner to the above, as a result of the measurements using the perspiration sensor and the blood flow sensor, if the user is slightly angry, "Slightly angry" is displayed.

Further, PTL 1 discloses a wristwatch-type conversation assistance device attached with a blood sensor having one or more painless needles. Blood is collected to measure a blood substance and to thus measure a change in emotion of the user. Then, a similar process to the above is performed.

Further, PTL 1 discloses an eyeglasses-type conversation assistance device in which a miniature camera and an eye camera are embedded. The miniature camera measures an eye blink and a facial expression. Further, the eye camera measures an eye movement and an eye blink. The eyeglasses-type conversation assistance device displays a result of information processing based on the measurement of an eye blink and a facial expression by the miniature camera and based on the measurement of an eye movement and an eye blink by the eye camera, on a transmission-type display inside a lens of the eyeglasses-type conversation assistance device lens, with characters and the like.

CITATION LIST

Patent Literature

PTL 1: Japanese Patent Application Publication No. 2005-46305

SUMMARY

However, the above conventional art needs to be further improved.

An aspect according to the present disclosure is a method for providing information in an information processing system, the method comprising:

acquiring, via a network, biogas information at multiple timings and time information corresponding to each of the multiple timings, wherein the biogas information represents a concentration of tetradecane of a user acquired by a sensor that detects tetradecane discharged from a skin surface of the user;

obtaining reference information representing an upper limit of a normal range of the concentration of tetradecane per unit period of time, using a memory storing the reference information representing the upper limit of the normal range;

determining a stress time period during which a concentration of the tetradecane of the user is more than the upper limit of the normal range, based on the acquired biological gas information; and outputting time period information indicating the determined stress time period to an information terminal of the user, to display the stress time period indicated by the time period information on a display of the information terminal.

The above aspect can achieve further improvement.

BRIEF DESCRIPTION OF DRAWINGS

FIG. 4 is a list of peak areas of tetradecane in the mass spectrum data by analyzing, with a gas chromatography/mass spectrometer (GC/MS), biogases collected during a stress task, after the stress task, during a relaxation task, and after the relaxation task.

FIG. 5 is a bar chart of average values and error ranges of the peak areas of tetradecane in the list of FIG. 4.

FIG. 6A is a graph showing prediction data of biological data dealt in a first embodiment of the present disclosure.

FIG. 6B is a graph showing prediction data of the biological data dealt in the first embodiment of the present disclosure.

FIG. 19 is a diagram showing an example of a sensor according to a variation of the present disclosure.

Figure 1:
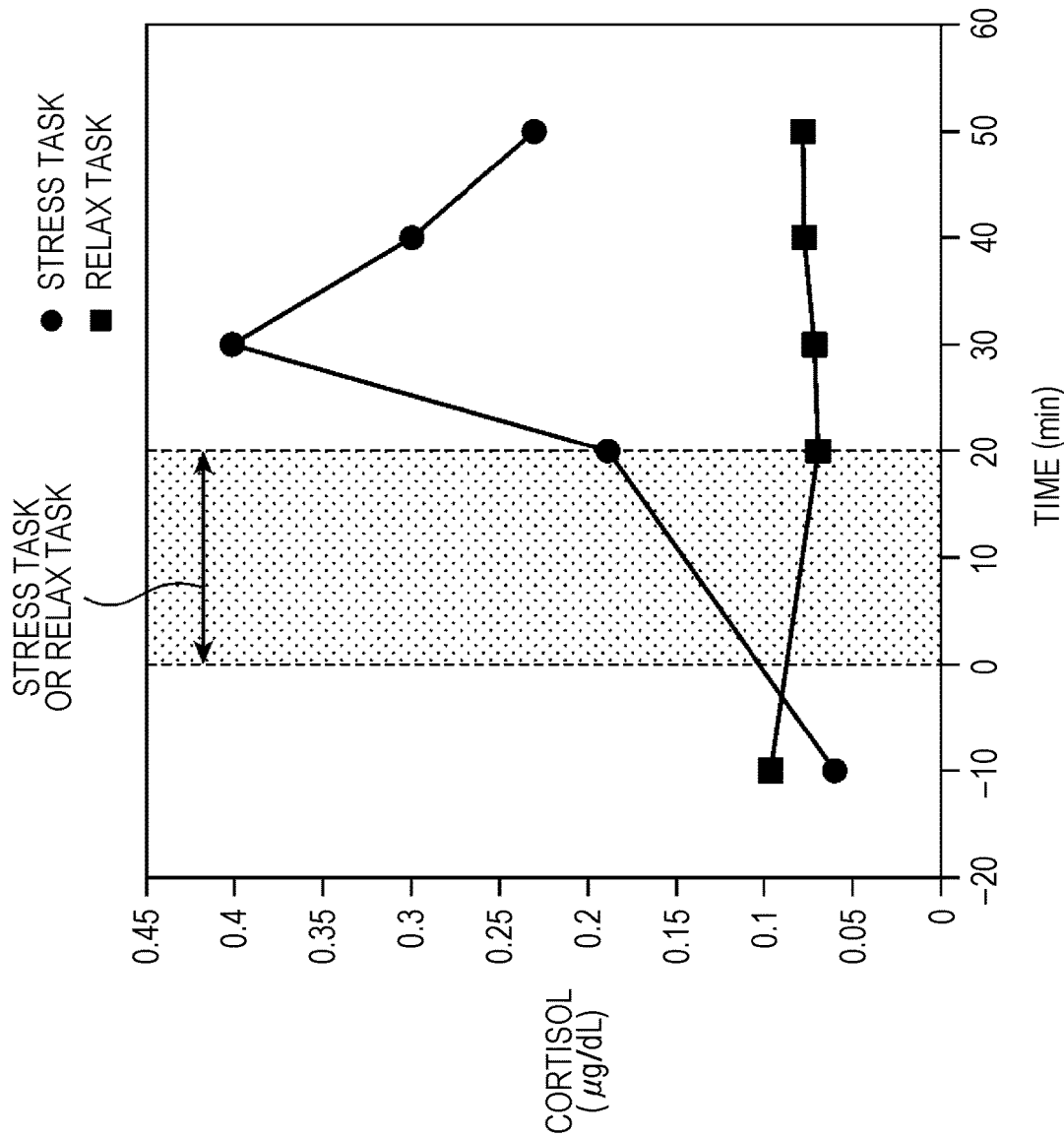
FIG. 1 is a graph showing temporal variations of concentrations of cortisol in saliva of an examinee before and after a stress task and before and after a relaxation task.

DESCRIPTION OF EMBODIMENTS (How an Aspect According to the Present Disclosure has been Conceived)

First, there will be described a point of observation of an aspect according to the present disclosure.

The present inventors are studying a method for objectively grasping invisible stress.

When a mental disorder such as depression occurs, the mental disorder is cured by a psychiatrist. The present inventors are studying how to grasp a sign of a mental disorder such as depression and to thus prevent a mental disorder before the mental disorder occurs.

The present inventors have a hypothesis that there is some causation between stress and depression. Stress is not necessarily harmful to mind and body. However, when stress is accumulated, the accumulated stress tends to give adverse effects to mind and body, and depression is thought to be one of the adverse effects.

Depression is classified, depending on the cause, into three types: (1) "somatogenic depression", (2) "endogenous depression", and (3) "psychogenic depression". The "somatogenic depression" is caused by characteristics of a brain or body organ or is caused by a drug. The "endogenous depression" has a genetic-level cause or has an inherent cause in a brain that causes a mental disorder. The "psychogenic depression" is caused by experiencing psychological stress. It is difficult to strictly sort out these three causes of depression, and it is also said that there is a high possibility that the three causes interact with each other to cause depression (Cabinet Office of Japan "White Paper on the National Lifestyle 2008" Chapter 1, Section 3 "2. Stress society and modern pathology", http://www5.cao.go.jp/seikatsu/whitepaper/h20/10_pdf/01_honpen/pdf/08sh_0103_03.pdf). Considering expectant women, it can be said that expectant women are under an environment where all of the above types (1) to (3) are easily satisfied. In a pregnancy period, because expectant women cannot take drugs and are restricted to exercise, it is difficult to work off stress. Therefore, there is a possibility that expectant women will develop mental disorders such as depression.

In addition, a report says that the postpartum depression tends to develop within two weeks after childbirth (Keiko Yoshida, "Understanding of mental problems with expectant women and Childcare Support" Honor lecture, General Academic meeting FY2013, The Okinawa Journal of Child Health 41 (2014): p. 3-8, http://www.osh.or.jp/in_oki/pdf/41gou/kouen.pdf). Therefore, it is important to grasp, during a pregnancy period, a sign of postpartum depression and to thus prevent postpartum depression. In addition, there is a possibility that not only expectant women but also ordinary people can develop a mental disorder such as depression due to work stress or the like.

In view of the above, the present inventors are studying on development of a tool for objectively grasping, before a mental disorder such as depression occurs, how much stress is accumulated on a person so that a mental disorder such as depression can be prevented beforehand.

A description will be given below to cortisol, which is generally well-known in association with stress. Cortisol is hormone whose secretion amount increases when excessive stress is applied. For this reason, by examining concentration of cortisol, it is possible to grasp a stress amount at the time of the examination. The concentration of cortisol can be measured by saliva sampling, blood sampling, or urine examination. For example, if urine collection is continued for 24 hours, it is also possible to measure cumulative cortisol secretion for one day and to thus evaluate a stress amount for one day.

If concentration of cortisol is high, Cushing's syndrome, stress, depression, anorexia nervosa, and other diseases are suspected. On the other hand, if concentration of cortisol is low, Addison's disease, congenital adrenal hyperplasia, adrenocorticotropic hormone (ACTH) insensitivity, pituitary-adrenocortical insufficiency, and other diseases are suspected.

As described above, the concentration of cortisol is effective to evaluate stress, but it is not realistic to continuously perform saliva sampling, blood sampling, or urine examination. Therefore, it is difficult to grasp a temporal variation of the above concentration of cortisol. Therefore, it is also difficult to grasp a temporal variation of stress of an examinee.

To address this issue, the present inventors set up a hypothesis that, as an evaluation index replacing the above cortisol, there is a biogas that is discharged from a skin surface of a person when stress is applied to mind and body. To prove the hypothesis through an experiment, the present inventors conducted an experiment to identify a biogas that has a correlation with stress.

Specifically, the present inventors made each of 30 examinees perform a task that made each examinee feel stress, and biogases were collected, in a specific period before and after performing the task, from an underarm and a hand of each examinee while saliva was collected from each examinee with predetermined time intervals. Then, from the saliva collected as described above, the present inventors draw graphs of temporal variations of the cortisol concentration to specify examinees whose temporal variations of the cortisol concentration were remarkable. The examinees specified above were identified to have had felt stress with the above task.

Next, the present inventors selected a plurality of biogases that seemed to have a correlation with stress, by analyzing about 300 types of biogases collected from the armpits of the examinees who felt stress in the above experiment. With respect to the thus selected biogases, by checking the discharge amounts of the biogases during and after performing the task, it was found that tetradecane was discharged from skins while the examinees felt stress. The description below will show in detail a procedure of the experiment until the above tetradecane was identified.

First, the present inventors built a psychology laboratory. The psychology laboratory had inside a small isolated room. The isolated room had only a glass window, through which it is possible to observe inside from outside. In addition, the isolated room was designed so that psychological pressure was applied to an examinee when the examinee did a stress task.

The present inventors introduced 30 examinees of Japanese women in their 20's to 40's into the above psychology laboratory, one examinee at a time. Then, the saliva of the examinee was collected in the psychology laboratory. In ten minutes after the saliva of the examinee was collected, the examinee worked on a stress task including computational problems and a speech for 20 minutes. In 30 minutes just after the end of the above stress task, the saliva of the examinee was collected totally four times, once in every 10 minutes. With respect to the thus collected saliva, the concentration of cortisol in each saliva sample was measured by using a salivary cortisol quantitative kit (Salimetrics, LLC.).

In addition, along with the above saliva sampling, biogases were collected from two places of the hand and the armpit of the examinee for 20 minutes during the stress task and for 20 minutes from 10 minutes to 30 minutes after the end of the stress task. The collection of biogases from a hand were performed as follows: the hand of an examinee was wrapped with a bag for sampling gases was fixed with a rubber band at a wrist part; and an absorbent for absorbing biogases was put in the bag. The collection of biogases from an armpit was performed by putting an absorbent under the armpit of an examinee. The absorbent put under the armpit was wrapped with cotton and was fixed with a bandage so that the absorbent could not be displaced under the armpit. The reason why biogases were collected from the hand and the underarm was that a hand and an underarm had high density of sweat glands. Biogases may be collected not only from the above hand and underarm but also from any part, as long as the biogases are collected from a skin surface.

On a day other than the day when the above stress task was performed, the saliva and the biogases of the examinees were each collected in the same procedure as on the day when the above stress task was performed except that a relaxation task was performed instead of the stress task. As the relaxation task in the experiment, each examinee only watched a natural scenery digital versatile disc (DVD).

FIG. 1 is a graph showing temporal variations of concentrations of cortisol in saliva of an examinee before and after a stress task and before and after a relaxation task. The vertical axis represents the concentration of cortisol (μg/dL), and the horizontal axis represents the time (minute) after the start of the stress task or the relaxation task. The higher side of the vertical axis of FIG. 1 represents the higher concentration of cortisol, and the higher concentration of cortisol represents that an examinee felt the higher stress as abovementioned. The shadowed part of the graph of FIG. 1 (from 0 minutes to 20 minutes on the horizontal axis) is a period during which the stress task or the relaxation task was performed. As a known fact, it is known that, in about 15 minutes after an examinee feels stress, the concentration of cortisol in saliva will increase.

With reference to the graph of FIG. 1, the concentration of cortisol increased rapidly at 20 minutes after the stress task was started (that is, immediately after the stress task was ended); however, there is almost no change in the concentration of cortisol between before and after the relaxation task. From this fact, it can be considered that the examinee whose concentration of cortisol showed the temporal variation of FIG. 1 felt stress with the stress task.

On the other hand, there was an examinee whose concentration of cortisol did not show such a temporal variation as that of FIG. 1. It can be considered that because such an examinee did not feel stress with the stress task, cortisol was not secreted in the saliva. Even if the biogases of the examinee who did not feel stress as described above are evaluated, it is impossible to grasp the causation between stress and biogases. Therefore, the examinees who did not feel stress were excluded from evaluation objects of biogases. In this way, from the 30 examinees, there were identified top 20 examinees (examinee Nos. 1 to 20) whose concentration of cortisol remarkably increased before and after the stress task.

Figure 2:
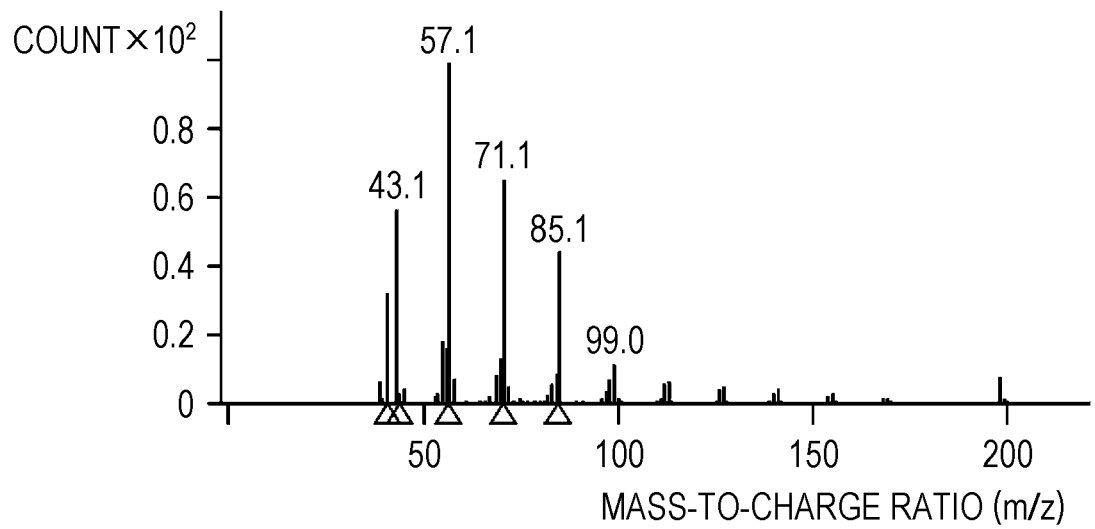
FIG. 2 is a mass spectrum data of tetradecane collected from an armpit of the examinee.
Figure 3:
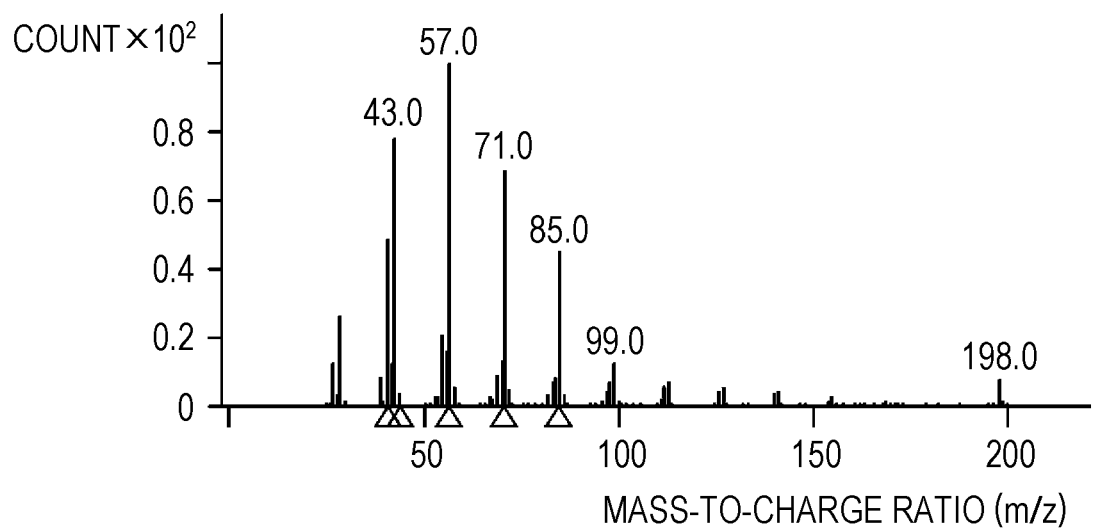
FIG. 3 is a mass spectrum data of tetradecane in National Institute of Standards and Technology (NIST) data base.

By heating the absorbents (during the stress task, after the stress task, during the relaxation task, and after the relaxation task) collected from the armpit of each of the above identified examinees, the biogases of each examinee absorbed in each absorbent were desorbed. By analyzing the above desorbed biogases with a gas chromatography-mass spectrometer (GC/MS manufactured by Agilent Technologies Japan, Ltd.), mass spectrum data of the biogases were obtained. By comparing the mass spectrum data with National Institute of Standards and Technology (NIST) data base by using analytical software of Agilent Technologies Japan, Ltd., tetradecane was identified. FIG. 2 shows mass spectrum data of tetradecane in biogas, and FIG. 3 shows mass spectrum data of tetradecane in the NIST data base. When the mass spectra of FIG. 2 and FIG. 3 are compared with each other, similar spectrum peaks were observed at almost identical mass-to-charge ratios (m/z). As described above, it was identified that tetradecane is contained as biogas.

Next, with respect to the above 20 examinees, the present inventors calculated a peak area of each of the biogases discharged from the underarm of each examinee (Examinee Nos. 1 to 20) during and after the stress task and during and after the relaxation task; and by comparing the peak area of a mass spectrum of each biogas between during and after the stress task and between during and after the relaxation task, a plurality of substances were chosen as candidates related to stress from more than 300 of biogas components. Of these candidate substances, tetradecane was apparently confirmed to have a correlation with stress. The chemical formula of tetradecane is shown below.

[Chemical formula 1]

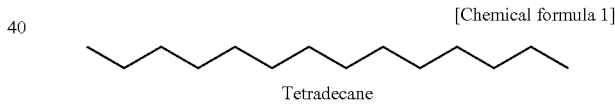

Tetradecane

Next, in the above-mentioned conditions, the peak areas of tetradecane were calculated from the mass spectra obtained with GC/MS. The table shown in FIG. 4 is a list of peak areas of tetradecane in the mass spectra obtained by analyzing, with GC/MS, the biogases discharged from the underarm of each examinee (Examinee Nos. 1 to 20) during the stress task, after the stress task, during the relaxation task, and after the relaxation task. The larger value of the peak area in the mass spectrum shown in FIG. 4 indicates that the larger amount of tetradecane was discharged from the armpit. FIG. 5 is a bar chart of average values and error ranges of the peak areas of tetradecane obtained from the list of FIG. 4.

With reference to FIG. 4 and FIG. 5, when the peak areas of tetradecane for the stress task were compared with the peak areas of tetradecane for the relaxation task, the peak areas of tetradecane were larger for the stress condition than for the relaxation condition. In addition, when the peak area of tetradecane during the stress task in FIG. 5 was compared with the peak area of tetradecane after the stress task, the peak area of tetradecane during the stress task was larger than the peak area of tetradecane after the stress task was ended. On the other hand, there was no remarkable difference observed in the peak area of tetradecane between during the relaxation task and after the relaxation task was ended.

From the above results, it has become clear that a larger amount of tetradecane was discharged from the underarms of the examinees during the stress task than during the relaxation task and that a larger amount of tetradecane was discharged from the underarms of the examinees during the stress task than after the stress task was ended. From these results, it can be said that the discharge amount of tetradecane has a correlation with the stress of the examinees. Therefore, tetradecane can be an index for objectively evaluating the stress amount of an examinee.

Based on the above experimental results, the present inventors identified that tetradecane is biogas resulting from stress. The present inventors believe that these knowledges did not exist before the present application.

Next, a device to detect tetradecane was developed, and the device made it possible to objectively grasp stress, which had been subjectively felt. That is, by using a method in which a device such as a sensor is used to measure tetradecane discharged from the skin surface of a human, continuous measurement can be done. In this case, it is possible to grasp when on a day a stress reaction occurred and what the person was doing when the stress reaction occurred. Thus, it is possible to objectively grasp a temporal variation of stress, and it is thus expected that stress can be controlled.

In addition, the present inventors have to lead achievement that stress can be objectively grasped by measuring the biogas resulting from stress, to a final goal of preventing a mental disorder such as depression. Each aspect of the invention according to the present disclosure relates to how to achieve the final goal.

Based on novel knowledge obtained as a result of the present inventors' hard studying, the present inventors have conceived the invention according to the following aspects.

An aspect according to the present disclosure is a method for providing information in an information processing system, the method comprising:

acquiring, via a network, biogas information at multiple timings and time information corresponding to each of the multiple timings, wherein the biogas information represents a concentration of tetradecane of a user acquired by a sensor that detects tetradecane discharged from a skin surface of the user;

obtaining reference information representing an upper limit of a normal range of the concentration of tetradecane per unit period of time, using a memory storing the reference information representing the upper limit of the normal range;

determining a stress time period during which a concentration of the tetradecane of the user is more than the upper limit of the normal range, based on the acquired biological gas information; and outputting time period information indicating the determined stress time period to an information terminal of the user, to display the stress time period indicated by the time period information on a display of the information terminal.

PTL 1 uses information such as perspiration, pulse, blood flow, eye blink, and facial expression. However, values indicated by the above information vary when a person goes up and down stairs. Therefore, although the above information is not irrelevant to stress, the information varies also due to causes irrelevant to stress. For this reason, the above information is not necessarily sufficient as a material for objectively determining a stress amount, and there is a possibility of erroneous determination.

In contrast, in the present aspect, a stress amount is objectively determined by using tetradecane, which is biogas that is supposed to have a relationship with stress. Therefore, it is possible to objectively grasp a degree of accumulation of stress without being affected by a subjective feeling of a person.

As a result, a time period when the concentration of tetradecane of the user exceeds the upper limit of the normal range is determined based on the acquired biogas information, and information indicating the determined time period is output to the information terminal of the user. This enables the person to objectively know a state of the person's own stress, and prevention of a mental disorder such as depression can thus be expected.

Further, in many cases, the user does not know what a stressor (stress factor) is to himself or herself. By displaying, on the information terminal, the time period when the upper limit of the normal range is exceeded, the user can look back on a day and objectively grasp how much stress the user felt on the day, for example. Further, in the present aspect, by taking as a clue what happened to the user in the time period when the upper limit of the normal range was exceeded, the user can find out the user's stressor.

As described above, it is possible to grasp when on a day a stress reaction occurred and what the user was doing when the stress reaction occurred, for example. Thus, it is possible to objectively grasp stress, and it is thus expected that stress can be controlled.

the upper limit of the normal range of the concentration of tetradecane per the unit period of time may be set for the user as individual information of the user, based on the biological gas information acquired in a predetermined period of time.

In this case, the user's own data is used as a standard value. The discharge amount of tetradecane, which is biogas, is affected by age, foods, body weight, and the like and has an individual variability; therefore, it is preferable to use the user's own data for accurate determination.

In contrast, PTL 1 does not disclose anything about how to hold reference information.

According to the present aspect, the user's own data is used as a standard value to determine a degree of stress. Therefore, an appropriate determination is possible for each person.

In addition, in the present aspect, the upper limit of the normal range of the concentration of tetradecane per the unit period of time may be used commonly to a plurality of users including the user.

In this case, since the standard value is commonly used for the plurality of users, it is possible to omit time and effort for generating and managing the standard value for each user.

Further, in the present aspect, the stress time period indicated by the time period information may be displayed in association with schedule information on the user, on the information terminal.

In this case, it is possible to easily check causation between stress and the user's own behavior by comparing the schedule information with the time period when stress was high.

Further, in the present aspect, the sensor for detecting tetradecane may be built in a device to be worn on the user.

In this case, since the sensor for detecting tetradecane is embedded in the device to be mounted on the user, it is possible to enable, for example, an object mounted on a user in a daily life to have a function of the sensor. As a result, it is possible to reduce hassle of the user wearing the sensor.

Further, in the present aspect, the time information corresponding to each of the multiple timings may be associated with each time when the sensor detects the biogas.

In this case, since it is determined, at a time when the biogas is obtained by the sensor, whether the concentration of tetradecane exceeds the upper limit of the normal range, it is possible to accurately notify the user of the time period when stress occurred. Note that, in the present aspect, "the time when the biogas was obtained" means that the time information may indicate the time when the sensor measured the biogas information or may indicate the time when a processing device such as a server acquired the biogas information from the sensor via a network.

An information processing system according to another aspect of the present disclosure includes:
a server device; and
an information terminal,
wherein the server device configured to:
acquire, via a network, biogas information at multiple timings and time information corresponding to time at each of the multiple timings, wherein the biogas information represents a concentration of tetradecane of a user acquired by a sensor that detects the tetradecane discharged from a skin surface of the user;
obtain reference information representing an upper limit of a normal range of the concentration of tetradecane per unit period of time, using a memory storing the reference information representing the upper limit of the normal range;
determine a stress time period during which a concentration of the tetradecane of the user is more than the upper limit of the normal range, based on the acquired biogas information; and
output time period information indicating the determined stress time period to the information terminal, and
wherein the information terminal displays the stress time period indicated by the time period information, on a display of the information terminal.

Further, an information terminal according to another aspect of the present disclosure may be used in the above information processing system.

Further, an information processing method according to another aspect of the present disclosure is a method for processing information using a computer, the method comprising:
acquiring, via a network, biogas information at multiple timings and time information corresponding to time at each of the multiple timings, wherein the biogas information represents a concentration of tetradecane of a user acquired by a sensor that detects tetradecane discharged from a skin surface of the user;
obtaining reference information representing an upper limit of a normal range of the concentration of tetradecane per unit period of time, using a memory storing the reference information representing the upper limit of the normal range;
determining a stress time period during which a concentration of the tetradecane of the user is more than the upper limit of the normal range, based on the acquired biogas information; and
outputting notice information representing that stress on the user is more than the upper limit of a predetermined normal range within the determined stress time period to display the notice information on a display.

In accordance with the present aspect, when the concentration of tetradecane exceeds the upper limit of the normal range, the information indicating that the stress of the user exceeds a normal range is displayed on the display. On the other hand, when the concentration of tetradecane is less or equal to the upper limit of the normal range, the information indicating that the stress of the user is within a normal range is displayed on the display. Therefore, it is possible to notify the user of an objective determination result indicating whether the user is in a stress state.

First Embodiment (Prediction Data)

FIGS. 6A and 6B are graphs each showing prediction data of biological data dealt in a first embodiment of the present disclosure. In each of FIGS. 6A and 6B, the vertical axis represents biogas concentration (an example of the biogas information), and the horizontal axis represents time. The prediction data does not represent actually measured biological data but just data made by predicting biological data. The biological data is the biological data measured by a sensor mounted on the user as will be mentioned below. The biological data represents measurement values of a concentration of a measurement object biogas (biogas concentration) of the biogases discharged from a skin surface of a user. In the present disclosure, the biogas to be the measurement object is tetradecane. A unit of the biogas concentration is μg/dL, for example.

FIG. 6A shows a temporal transition of the biological data of the user when no stress is applied, and FIG. 6B shows a temporal transition of the biological data of the user when stress is applied. As shown in FIG. 6A, regarding the biological data when no stress is applied, the biogas concentration is within the normal range. On the other hand, as shown in FIG. 6B, regarding the biological data when stress is applied, a frequency with which the biogas concentration exceeds an upper limit DH of the normal range is higher. In the example of FIG. 6B, the biogas concentration exceeds the upper limit DH four times in a time period from 06:00 to 24:00.

In the present disclosure, the time period when the biogas concentration exceeds the upper limit DH is determined, and the information indicating the determined time period is notified to the user, so that a mental disorder such as depression is prevented.

(Sensor)

Figure 7:
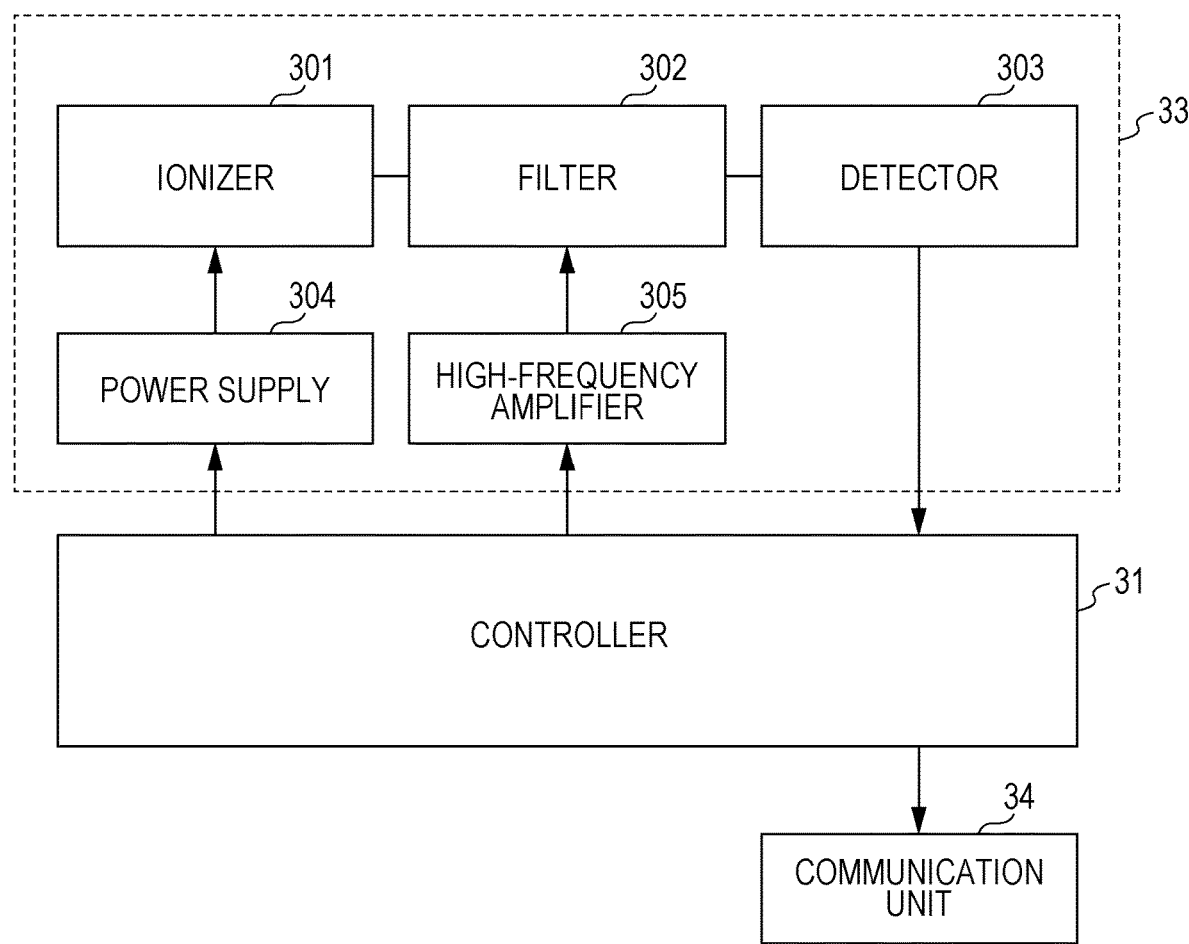
FIG. 7 is a block diagram showing an example of a configuration of a sensor for measuring biological data in the first embodiment of the present.

FIG. 7 is a block diagram showing an example of a configuration of sensor 3 that measures the biological data in the first embodiment of the present disclosure.

As sensor 3, in the present disclosure, there is used a sensor using, for example, the technology of Field Asymmetric Ion Mobility Spectrometry (FAIMS). The field asymmetric ion mobility spectrometer is used to selectively separate one type of substance from a mixture including two or more types of substances.

Sensor 3 includes detection unit 33, controller 31, and communication unit 34. Detection unit 33 includes ionizer 301, filter 302, detector 303, power supply 304, and high-frequency amplifier 305. Note that, in FIG. 7, the arrowed lines show flows of electric signals, and the lines connecting among ionizer 301, filter 302, and detector 303 show flow of the biogas.

Power supply 304 and high-frequency amplifier 305 are respectively used to drive ionizer 301 and filter 302. From the biogas ionized by using ionizer 301, only an intended biogas (tetradecane in the present disclosure) is separated with filter 302, and an amount of ions having passed through filter 302 is detected by detector 303, so that information indicating the biogas concentration is obtained. The obtained information is output via communication unit 34. Controller 31 controls driving of sensor 3.

Figure 8:
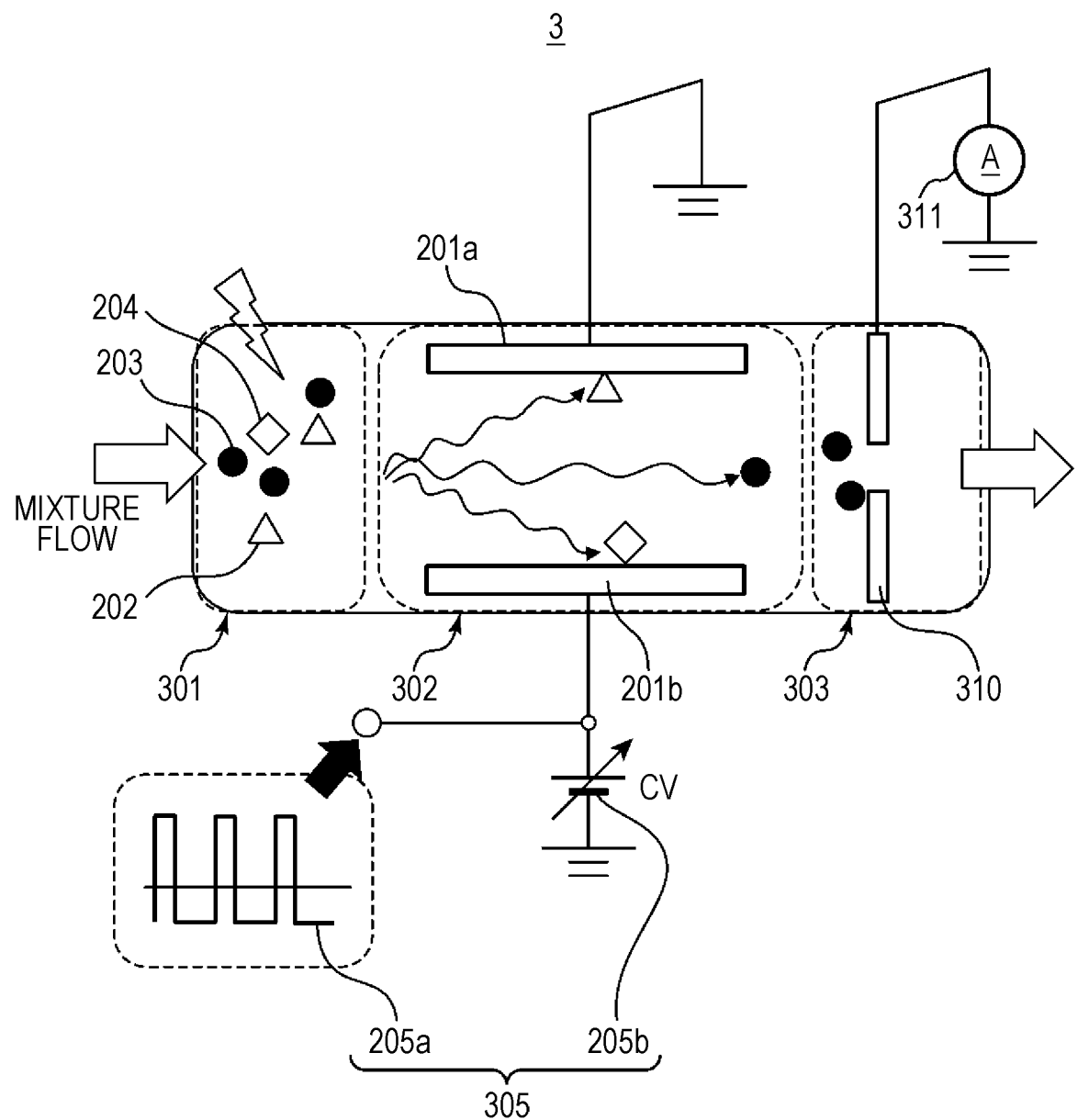
FIG. 8 is a diagram illustrating in more detail an operation of the sensor shown in FIG. 7.

FIG. 8 is a diagram illustrating in more detail an operation of sensor 3 shown in FIG. 7. A mixture supplied to ionizer 301 is the biogas discharged from the skin surface of the user. Ionizer 301 may include an inlet for taking in the biogas having been discharged from the skin surface of the user. Further, the inlet may be provided with an absorbent for absorbing the biogas. In addition, a heater may be provided to desorb the biogas absorbed in the absorbent from the absorbent. In the example of FIG. 8, the mixture is supposed to include three types of gases 202 to 204 for the purpose of description. Gases 202 to 204 are ionized by using ionizer 301.

Ionizer 301 includes a corona discharge source, a radiation source, and other units and ionizes gases 202 to 204. Ionized gases 202 to 204 are supplied to filter 302 disposed adjacent to ionizer 301. Note that the corona discharge source and the radiation source constituting ionizer 301 are driven by a voltage supplied from power supply 304.

Filter 302 includes first electrode 201a and second electrode 201b each provided parallel to each other and having a flat plate shape. First electrode 201a is grounded. On the other hand, second electrode 201b is connected to high-frequency amplifier 305.

High-frequency amplifier 305 includes AC voltage source 205a for generating an asymmetric AC voltage and variable voltage source 205b that generates a compensation voltage CV, which is a DC voltage. AC voltage source 205a generates the asymmetric AC voltage and applies the asymmetric AC voltage to second electrode 201b. One end of variable voltage source 205b is connected to second electrode 201b, and the other end is grounded. With this arrangement, the asymmetric AC voltage generated by AC voltage source 205a is superposed with the compensation voltage CV and is supplied to second electrode 201b.

Between first electrode 201a and second electrode 201b, three types of gases 202 to 204 having been ionized are supplied. Three types of gases 202 to 204 are influenced by the electric field generated between first electrode 201a and second electrode 201b.

Figure 9:
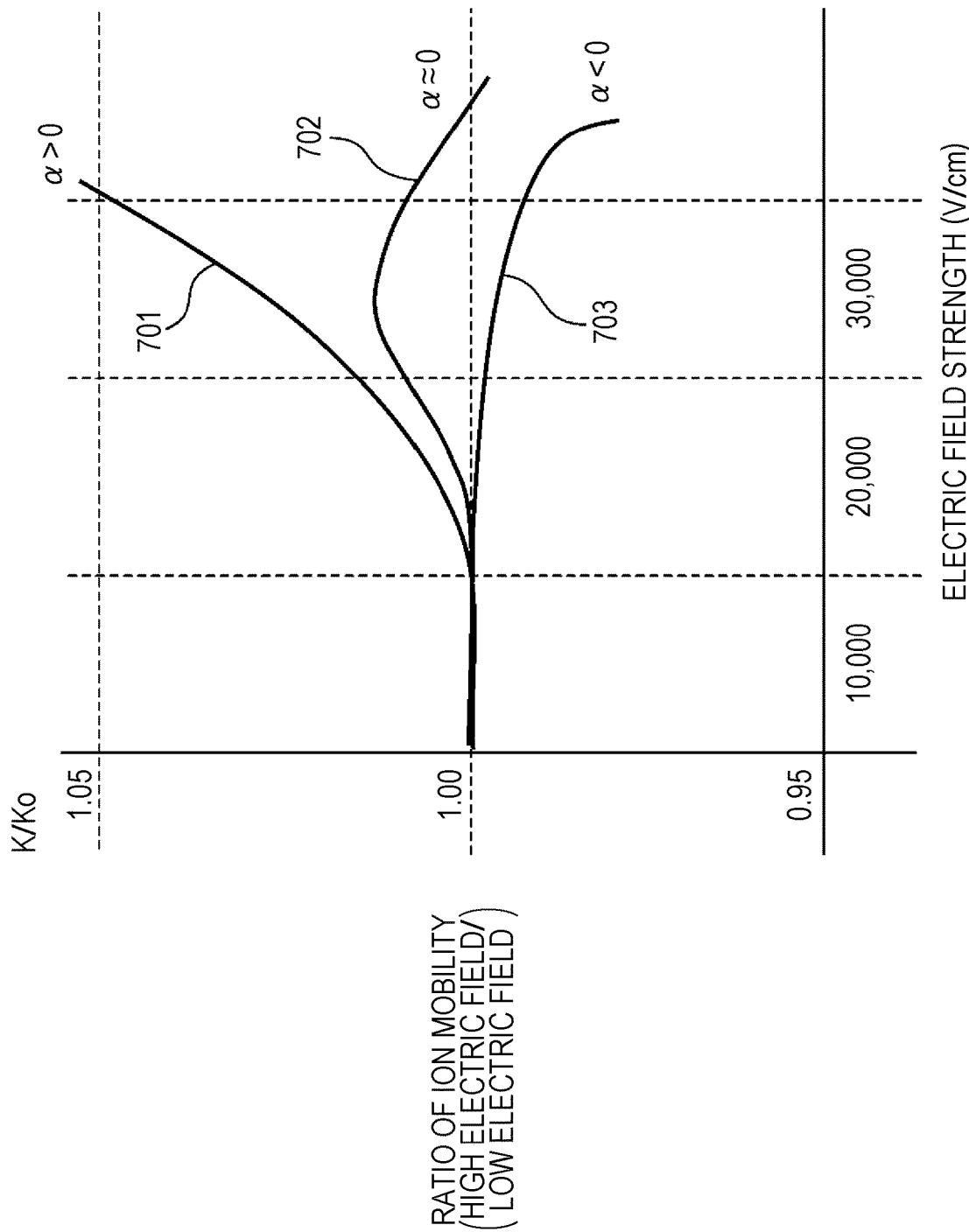
FIG. 9 is a graph showing a relationship between an electric field intensity and a ratio of ion mobility.

FIG. 9 is a graph showing a relationship between an electric field intensity and a ratio of ion mobility, the vertical axis represents the ratio of ion mobility, and the horizontal axis represents the electric field intensity (V/cm). The coefficient $\alpha$ depends on the type of ion. The ratio of ion mobility represents the ratio of the mobility in high electric fields to the ion mobility in the small electric field limit.

As represented by curved line 701, the ionized gas with a coefficient $\alpha>0$ moves more actively when the electric field intensity increases. The ion having a mass-to-charge ratio smaller than 300 moves in this way.

As represented by curved line 702, the ionized gas with the coefficient $\alpha$, which is almost 0, moves more actively when the electric field intensity increases; however, the mobility of the ionized gas decreases when the electric field intensity further increases.

As represented by curved line 703, the mobility of the ionized gas with the coefficient $\alpha$, which is negative, decreases when the electric field intensity increases. An ion having a mass-to-charge ratio of greater than or equal to 300 moves in this way.

Because of the differences between the mobilities, three types of gases 202 to 204 move in different directions inside filter 302 as shown in FIG. 8. In the example of FIG. 8, only gas 203 is discharged from filter 302. On the other hand, gas 202 is trapped by a surface of first electrode 201a, and gas 204 is trapped by a surface of second electrode 201b. In this way, from three types of gases 202 to 204, only gas 203 is selectively separated and is discharged from filter 302. That is, on sensor 3, when the electric field intensity is appropriately set, an intended gas can be discharged from filter 302. Note that the electric field intensity is determined by the voltage value of the compensation voltage CV and a waveform of the asymmetric AC voltage generated by AC voltage source 205a. Therefore, sensor 3 can discharge the biogas to be the measurement object from filter 302 by setting the voltage value of the compensation voltage CV and the waveform of the asymmetric AC voltage to a predetermined voltage value and waveform, depending on the type (tetradecane in the present disclosure) of the biogas to be the measurement object.

Detector 303 is disposed adjacent to filter 302. In other words, filter 302 is disposed between ionizer 301 and detector 303. Detector 303 includes electrode 310 and ammeter 311 to detect gas 203 having passed through filter 302.

Gas 203 having reached detector 303 delivers an electric charge to electrode 310. The value of a current flowing in proportion to the amount of the delivered electric charge is measured by ammeter 311. From the value of the current measured by ammeter 311, the concentration of gas 203 is measured.

(Network Configuration)

Figure 10:
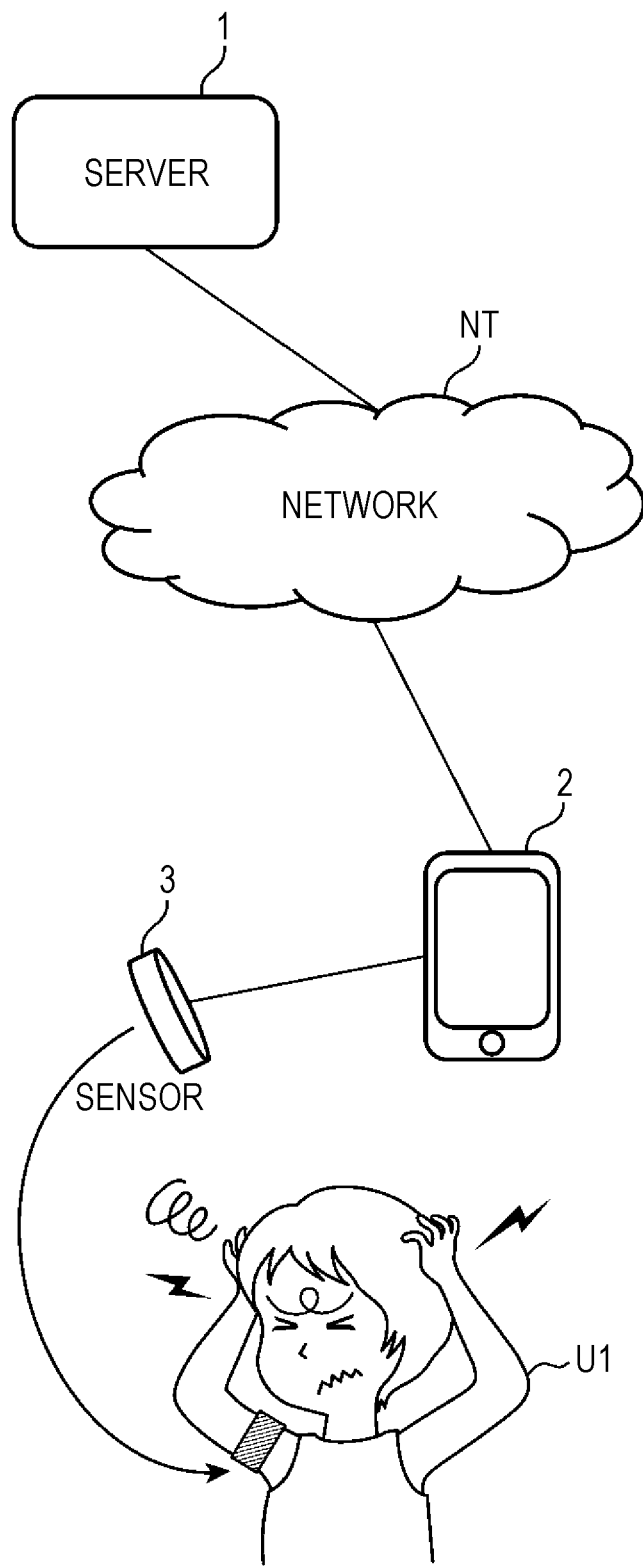
FIG. 10 is a diagram showing an example of a network configuration of an information processing system according to the first embodiment of the present disclosure.

FIG. 10 is a diagram showing an example of a network configuration of the information processing system according to the first embodiment of the present disclosure. The information processing system provides a care service for taking care of stress of user U1. This care service is provided by, for example, an insurance company or the like with which user U1 is contracted. Note that the care service may be actually performed by, for example, a manufacturer that manufactures sensor 3 and that is subcontracted by the insurance company. Alternatively, the care service may be provided by a service provider different from the insurance company that provides the care service itself.

The insurance company provides user U1 with an insurance service such as life insurance and medical insurance. In this case, the insurance company prevents diseases resulting from a mental disorder of user U1 by, for example, lending sensor 3 to user U1, acquiring biological data of user U1 and managing a stress state of user U1. This enables the insurance company to save spending of insurance money. Since this care service forces user U1 to wear sensor 3, some users U1 feel a burden. To address this issue, the insurance company may provide an insurance plan in which an insurance fee to be paid by user U1 is discounted in exchange for this care service.

The information processing system includes server 1 (an example of the server device), user terminal 2 (an example of the information terminal), and sensor 3.

Server 1 and user terminal 2 are communicably connected to each other via network NT. Network NT is configured with a network including an internet communication network, a portable telephone communication network, and a public telephone line network. Sensor 3 and user terminal 2 are communicably connected to each other via short-range wireless communication such as wireless local area network (LAN) of IEEE802.11b, Bluetooth (registered trade mark, IEEE802.15.1), or the like.

Server 1 is configured with, for example, a cloud server including one or more computers. Server 1 includes: a processor such as a central processing unit (CPU), a field programmable gate array (FPGA), or the like; and a memory. Server 1 acquires the biological data of user U1 measured by sensor 3 via user terminal 2 and network NT, and determines whether the biogas concentration is within the normal range.

User terminal 2 is configured with a portable information processing device such as a smartphone, a tablet terminal, or the like. However, user terminal 2 may be configured with a stationary computer. User terminal 2 is held by user U1.

Sensor 3 is mounted on, for example, an arm of user U1 and detects the concentration of the biogas discharged from an underarm of user U1. Sensor 3 includes, for example, a fitting belt, and a user winds the fitting belt around the arm at a position close to the underarm, so that sensor 3 is attached in the vicinity of the underarm. This arrangement enables sensor 3 to detect the biogas discharged from the underarm. As the position, on the arm, in the vicinity of the underarm, it is possible to employ, for example, a position that is on the arm and is slightly close to the elbow from a connection point between the body and the arm. Note that when it is considered that the biogas is discharged much from the underarm, sensor 3 is preferably attached, for example, in such a manner that the inlet for collecting the biogas is located on the rear side of the arm. In this case, the reason why sensor 3 is attached at the position, on the arm, in the vicinity of the underarm is that it is difficult to attach sensor 3 to the underarm itself. However, this is an example. For example, sensor 3 may be attached to an underarm part of a shirt to be put on user U1. This arrangement enables sensor 3 to face the underarm, and the biogas can be more surely collected. Note that this shirt is an example of the device to be mounted on a user.

Figure 11:
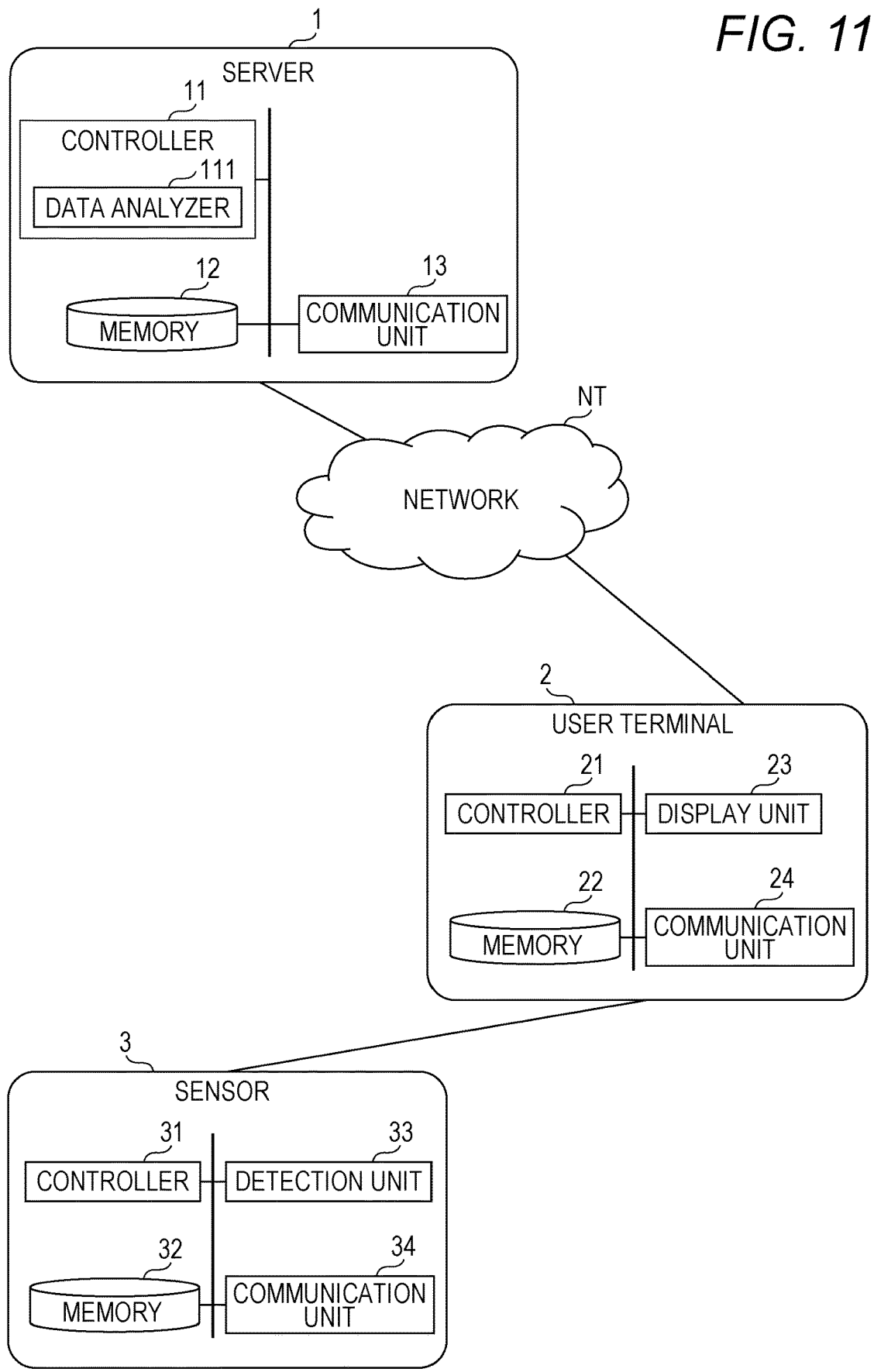
FIG. 11 is a block diagram showing an example of a detailed configuration of the information processing system shown in FIG. 10.

FIG. 11 is a block diagram showing an example of a detailed configuration of the information processing system shown in FIG. 10. Server 1 includes controller 11, memory 12, and communication unit 13. Controller 11 is configured with a processor and includes data analyzer 111. Data analyzer 111 is realized by, for example, a processor executing a program making a computer execute an information provision method, of the present disclosure, stored in memory 12. Note that the program making a computer execute an information provision method of the present disclosure may be provided by download through a network or may be provided by way of a computer-readable non-volatile recording medium storing the program.

If communication unit 13 receives the biological data obtained by sensor 3, data analyzer 111 acquires the biological data from communication unit 13. Then, data analyzer 111 reads out from memory 12 the information indicating the upper limit DH of the normal range of the biogas concentration, and determines a time period when the biogas concentration indicated by the biological data exceeds the upper limit DH. Then, data analyzer 111 registers the biological data in biological data table T4 (FIG. 12) stored in memory 12, in association with a result of the determination. Further, when the biological data has been accumulated for a prescribed period (for example, one day, half a day, two days, one week, or one month), data analyzer 111 transmits, to user terminal 2 via communication unit 13, the information indicating the time period when the biogas concentration in the biological data in the prescribed period exceeded the upper limit DH (hereinafter, the information is described as "time period information").

Figure 12:
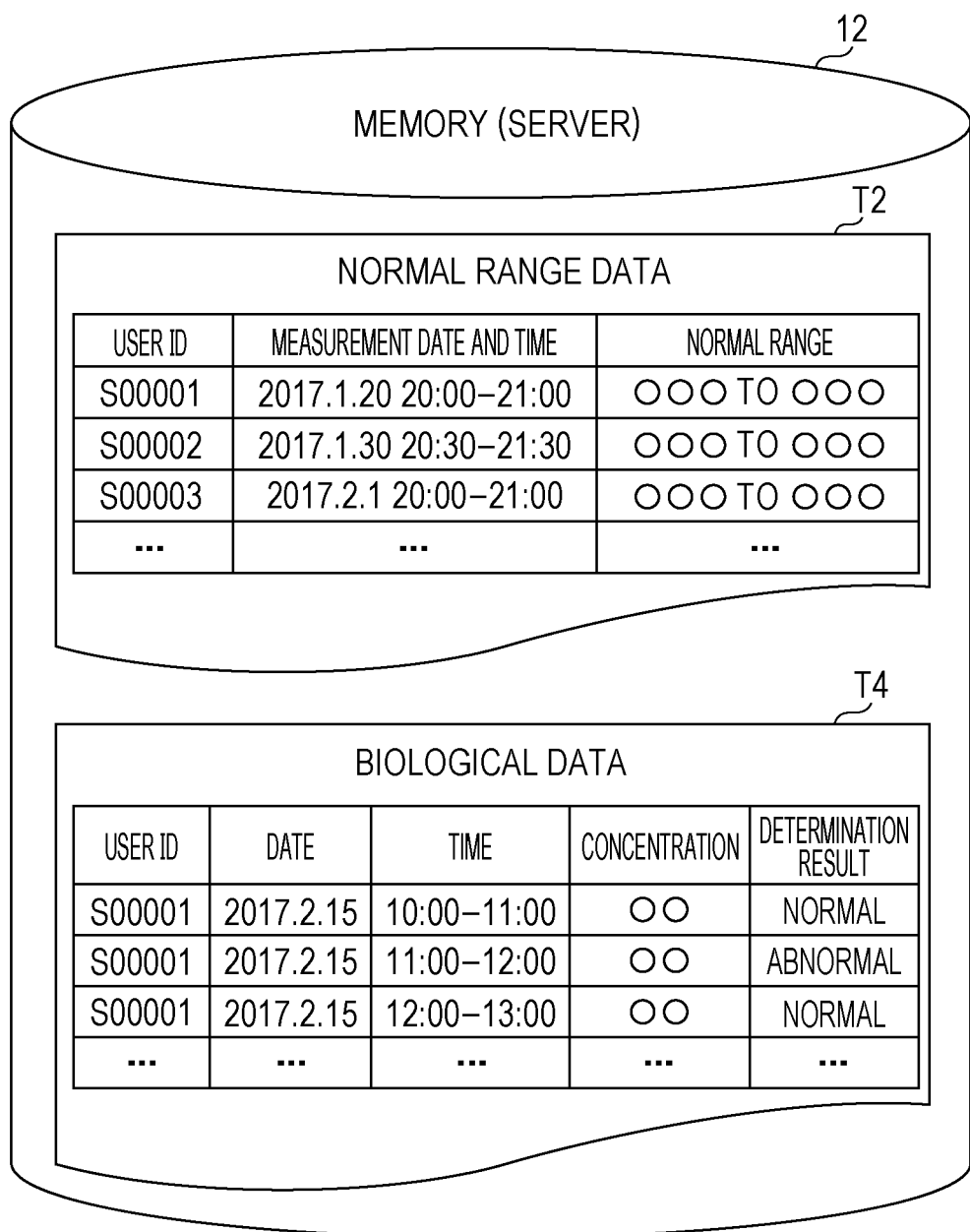
FIG. 12 is a diagram showing an example of data configurations of tables stored in a memory.

Memory 12 stores information indicating the normal range of the biogas concentration. In the present disclosure, as shown in FIG. 12, memory 12 stores normal range data table T2 and biological data table T4. FIG. 12 is a diagram showing an example of data configurations of the tables stored in memory 12.

Normal range data table T2 stores the normal ranges of stress of the biogas concentrations of one or more users who receive a care service. In normal range data table T2, one record is assigned to one user, and "user ID", "measurement date and time", and "normal range" are stored in association with each other.

In a "user ID" field, there is stored an identifier for uniquely identifying a user who receives a care service. In a "measurement date and time" field, there is stored a time period corresponding to a measurement date and time of the biological data used to calculate the normal range. In a "normal range" field, there is stored the normal range calculated by using the biological data stored in the "measurement date and time" field. In the "normal range" field, there are stored a lower limit DL and an upper limit DH of the normal range.

For example, regarding a user with the user ID "S00001", the normal range is calculated by using the biological data measured in the time period from 20:00 to 21:00 on Jan. 20, 2017.

As described above, in the present disclosure, since the normal range is already calculated for each user, stress can be determined for each user by using the normal range appropriate to each user, so that determination accuracy can be improved. In the present disclosure, the normal range is calculated for each user, but this is just an example, and it is possible to use an average value of the normal ranges calculated for a part of all the users, as the normal range for all the users. Alternatively, an average value of the normal ranges of all the users may be used as the normal range for all the users. In these cases, it is not necessary to store or calculate the normal range for each user, and it is thus possible to save memory consumption and to reduce process steps.

Biological data table T4 stores the biological data obtained by sensor 3. In biological data table T4, one record is assigned to one piece of biological data, and "user ID", "date", "time", "concentration", and "determination result" are stored in association with each other.

In a "user ID" field, there is stored a user ID that is the same as the user ID stored in normal range data table T2. In a "date" field, there is stored a measurement date of the biological data. In a "time" field, there is stored the time period when the biological data was measured. In a "concentration" field, there is stored the biogas concentration indicated by the biological data. In a "determination result" field, there is stored the determination result whether the biogas concentration is within the normal range. Note that in the "time" field, there may be stored the time period when the biological data was acquired by server 1.

For example, in the record on the first row of biological data table T4, there is stored the biological data, which is the biogas concentration "OO", of the user with the user ID "S00001" measured in the time period 10:00 to 11:00 on Feb. 15, 2017. In addition, in the record on the first row, there is "Normal" stored in the "Determination result" field because the biogas concentration is within the normal range. On the other hand, in the record on the second row, there is stored "Abnormal" in the "Determination result" field because the biogas concentration was out of the normal range.

Note that biological data table T4 shows only the biological data of the user with the user ID "S00001". However, this is just an example, and in biological data table T4 there is stored the biological data of all of the users who receive a care service.

Refer back to FIG. 11 again. Communication unit 13 is configured with, for example, a communication circuit that connects server 1 to network NT, and communication unit 13 receives the biological data measured by sensor 3 and transmits the time period information to user terminal 2.

User terminal 2 includes controller 21, memory 22, display unit 23 (an example of the display), and communication unit 24. Controller 21 is configured with a processor such as a CPU, and performs overall control of user terminal 2. Memory 22 stores various types of data. In the present disclosure, memory 22 stores, in particular, an application to be performed on user terminal 2 to make user U1 receive a care service. In addition, memory 22 stores the user ID in association with biological data.

Display unit 23 is configured with, for example, a display including a touch panel, and displays various types of information. In the present disclosure, display unit 23 displays, in particular, the time period information. Communication unit 24 is configured with a communication circuit that connects user terminal 2 to network NT and, at the same time, makes user terminal 2 communicate with sensor 3. In the present disclosure, communication unit 24 receives, in particular, the biological data transmitted from sensor 3 and transmits the received biological data to server 1 in association with the user ID stored in memory 22. Further, in the present disclosure, communication unit 24 receives, in particular, the time period information transmitted from server 1. Note that display unit 23 does not have to be configured with a touch panel. In this case, user terminal 2 only has to include an operation unit to receive an operation from the user.

Sensor 3 includes controller 31, memory 32, detection unit 33, and communication unit 34. Controller 31 is configured with a processor such as a CPU or a digital signal processor (DSP), and performs overall control of sensor 3. Memory 32 temporarily stores, for example, the biological data measured by detection unit 33. In addition, memory 32 stores data (for example, a frequency and amplitude on the positive side and amplitude on the negative side) that is necessary for AC voltage source 205a to generate the asymmetric AC voltage. Further, memory 32 stores a voltage value of the compensation voltage CV.

Communication unit 34 is configured with a communication circuit for wireless LAN, Bluetooth (registered trade mark), or the like, and transmits the biological data measured by detection unit 33 to user terminal 2. This biological data is received by communication unit 24 of user terminal 2 and is transmitted to server 1 via network NT.

(Sequence)

Figure 13:
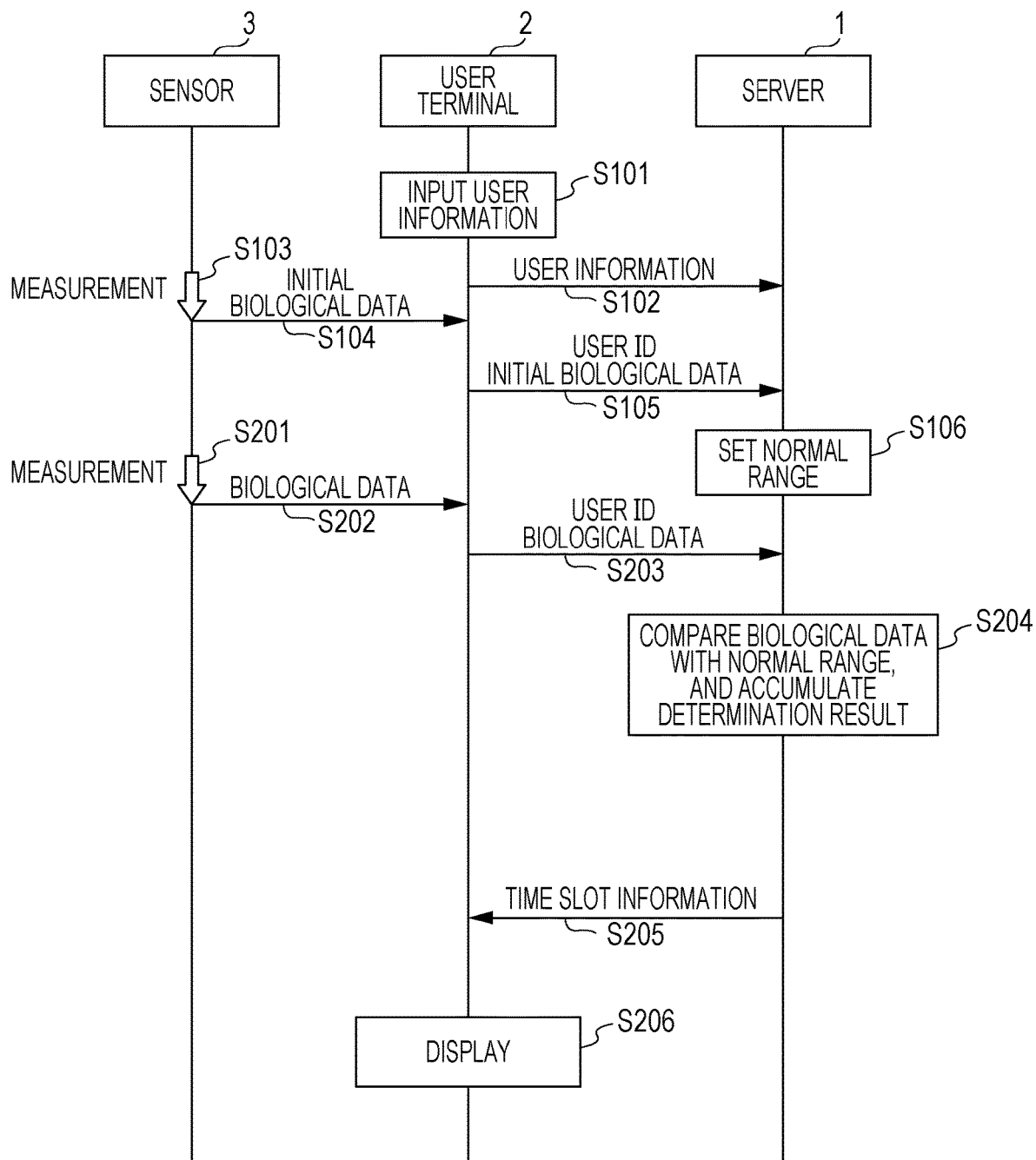
FIG. 13 is a sequence diagram showing an example of a process in a biological information system shown in FIG. 11.

FIG. 13 is a sequence diagram showing an example of a process in the biological information system shown in FIG. 11. This sequence diagram is divided into an initial phase from step S101 to step S106 and a normal phase including step S201 and the steps subsequent thereto. The initial phase is for calculating the normal range of a user and is performed immediately after the care service is introduced. The normal phase is for monitoring the stress state of a user by using the normal range calculated in the initial phase.

The initial phase is performed, for example, when the application for user terminal 2 for receiving the care service is started on user terminal 2 by a user for the first time.

First, display unit 23 of user terminal 2 receives input of user information (step S101). In this step, display unit 23 may allow the user to input user information by displaying a registration screen to allow the user to input the user information such as a user ID, a telephone number, an e-mail address, an SNS account, and the like. Here, as the user ID, it is possible to use the user ID issued when the user makes an insurance contract with an insurance company, for example. Alternatively, the user ID may be the user ID issued by server 1 and notified to user terminal 2 when server 1 receives the user information in step S102 to be described later. In this case, the user does not have to input a user ID on the registration screen.

Next, controller 21 of user terminal 2 transmits the user information having been input to server 1 by using communication unit 24 (step S102). The transmitted user information is stored, by controller 41 of server 1, in a user information table (not shown) that manages user information of one or more users who receives a care service.

Next, detection unit 33 of sensor 3 measures the initial biological data of the user (step S103). Next, controller 31 of sensor 3 transmits the measured initial biological data to user terminal 2 by using communication unit 34 (step S104).

On user terminal 2, if communication unit 24 receives the initial biological data, controller 21 transmits the initial biological data to server 1 in association with the user ID (step S105).

Because the initial biological data is used to calculate the normal range of the user, it is a precondition that the user is not in a stress state. For this reason, after the transmission of the user information is finished (step S102), user terminal 2 may cause display unit 23 to display, for example, a message such as "Biological data will be measured. Please wear the sensor and stay calm for a while". Data analyzer 111 of server 1 sets the normal range (step S106). The normal range having been set is stored in normal range data table T2 in association with the user ID by data analyzer 111 of server 1.

This completes the initial phase. Subsequently, the normal phase will be performed.

First, on sensor 3, detection unit 33 measures biological data (step S201), and controller 31 transmits the biological data to user terminal 2 by using communication unit 34 (step S202).

Next, on user terminal 2, if communication unit 24 receives the biological data, controller 21 transmits the biological data to server 1 by using communication unit 24 in association with the user ID (step S203).

Next, on server 1, if communication unit 13 receives the biological data, data analyzer 111 compares the biological data with the normal range and accumulates the determination result (step S204). In this step, the determination result is accumulated in the "determination result" field in the record for the concerning user in normal range data table T2, by using the user ID as a key.

Next, when a prescribed period has elapsed, data analyzer 111 transmits, to user terminal 2 by using communication unit 13, the time period information about the time period when the biogas concentration exceeded the upper limit of the normal range in the prescribed period (step S205).

Next, on user terminal 2, when communication unit 24 receives the time period information, controller 21 displays the time period information on display unit 23 (step S206).

Note that if the prescribed period has not elapsed, the process of step S205 and the steps subsequent thereto is not performed, and the process of steps S201 to S204 is repeated.

Figure 14:
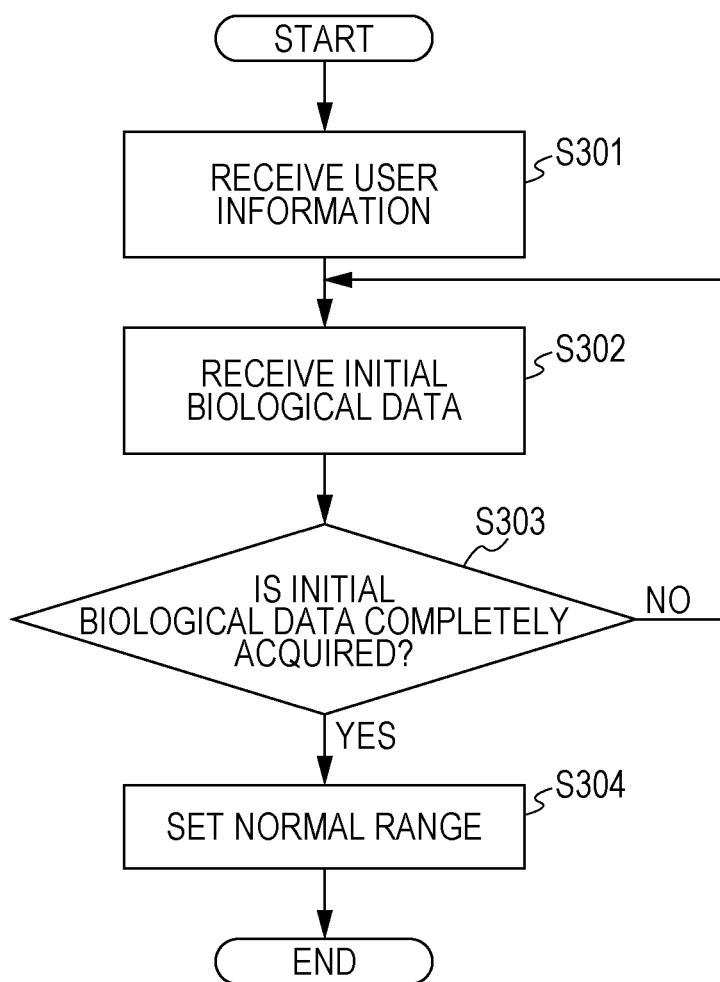
FIG. 14 is a flowchart showing details of an initial phase process according to the first embodiment of the present disclosure.

FIG. 14 is a flowchart showing details of the initial phase process according to the first embodiment of the present disclosure. The flowchart is executed on server 1. First, communication unit 13 receives the user information transmitted from user terminal 2 (step S301).

Next, communication unit 13 receives the initial biological data transmitted from user terminal 2 (step S302). Next, if the initial biological data is not completely acquired (step S303: NO), data analyzer 111 returns the process back to step S302. On the other hand, if the initial biological data is completely acquired (step S303: YES), data analyzer 111 proceeds the process to step S304. In this process, data analyzer 111 may finish acquisition of the initial biological data if the number of pieces of received initial biological data reaches a predetermined number sufficient to calculate the normal range or if a predetermined measurement period has elapsed since start of measurement of the initial biological data. In the present disclosure, as the measurement period for the initial phase, one hour, two hours, three hours, one day, two days, three days, or the like is used, for example, although depending on the measurement interval for the biological data. For example, if the measurement interval for the biological data is short, many pieces of initial biological data can be obtained in a short time, and the measurement period for the initial biological data can be accordingly reduced. For example, if one hour is used as the measurement interval for the biological data, half a day, one day, two days, three days, or the like is used as the measurement period for the initial biological data, for example. If one minute or one second is used as the measurement interval for the biological data, ten minutes, 20 minutes, one hour, two hours, three hours, or the like is used as the measurement period for the initial biological data, for example. However, these numerical values are just examples and can be changed appropriately.

Note that the measurement period for the initial biological data corresponds to an example of the predetermined period of time.

Next, data analyzer 111 sets the normal range by using the obtained initial biological data (step S304). Suppose, for example, the initial biological data as shown in FIG. 6A is obtained. In this case, data analyzer 111 extracts an upper limit peak and a lower limit peak of the biogas concentration by analyzing the obtained initial biological data. Then, data analyzer 111 may calculate a value as the upper limit DH by adding a predetermined margin to the upper limit peak, and may calculate a value as the lower limit DL by subtracting a predetermined margin from the lower limit peak. Alternatively, data analyzer 111 may calculate a value as the upper limit DH by adding a predetermined margin to an average value of the upper-side peaks, and may calculate a value as the lower limit DL by subtracting a predetermined margin from an average value of the low-side peaks. By the above process, the normal range is set for each user.

Figure 15:
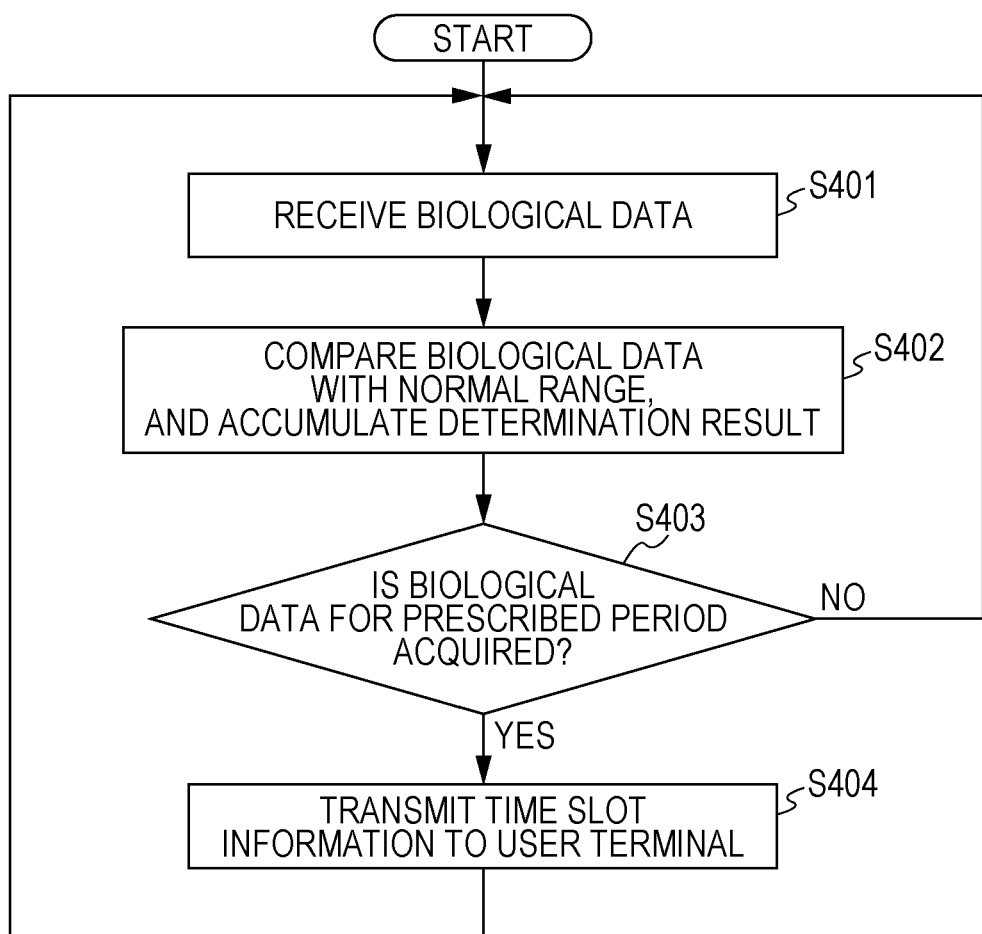
FIG. 15 is a flowchart showing details of a process of a normal phase according to the first embodiment of the present disclosure.

FIG. 15 is a flowchart showing details of the process of the normal phase according to the first embodiment of the present disclosure. Note that, the flowchart of FIG. 15 is periodically executed on server 1 at the measurement intervals of sensor 3 measuring the biological data.

First, communication unit 13 receives the biological data from user terminal 2 (step S401). Next, data analyzer 111 determines whether the stress state is normal or abnormal, by comparing the biogas concentration indicated by the biological data to the normal range for the concerning user, and data analyzer 111 accumulates the determination result in biological data table T4 (step S402). In detail, data analyzer 111 may store, in biological data table T4, the determination result in association with the user ID, the measurement date and time, and the biogas concentration. Now refer to biological data table T4 of FIG. 12. On the record on the first row, there are written "2017.2.15" on the "date" field and "10:00-11:00" on the "time" field. This is because the measurement interval for the biological data is set to one hour and this biological data was measured between 10:00 and 11:00 on Feb. 15, 2017.

In the present disclosure, as the biogas of the measurement object, tetradecane is used. Tetradecane has a positive correlation with intensity of stress. Therefore, data analyzer 111 may determine, if the biogas concentration is greater than the upper limit DH of the normal range, that the stress state is abnormal and, if the biogas concentration is lower than or equal to the upper limit DH, that the stress state is normal.

Next, if data analyzer 111 acquires the biological data for the prescribed period (one day, for example) (step S403: YES), data analyzer 111 proceeds the process to step S404, and if data analyzer 111 does not acquire the biological data for one day (step S403: NO), data analyzer 111 turns the process back to step S401 and acquires the biological data to be measured next.

In this process, in a case where one day is used as the prescribed period, when it becomes "00:00", data analyzer 111 may determine YES in step S403 and deal with the biological data for one day obtained on the previous day, as the biological data to be processed.

Next, data analyzer 111 transmits the time period information to user terminal 2 by using communication unit 13 (step S404). In this step, data analyzer 111 may transmit data indicating a temporal transition of the biogas concentration obtained in the prescribed period and the time period when the biogas concentration got out of the normal range, by embedding the data indicating the temporal transition and the time period, in the time period information. In this step, as the timing when time period information is transmitted, a predetermined time (for example, 07:00) in the next morning may be used, for example. When step S404 is finished, the process goes back to step S401.

By the above process, it is determined whether stress exceeded the normal range.

(Time Period Information)

Figure 16:
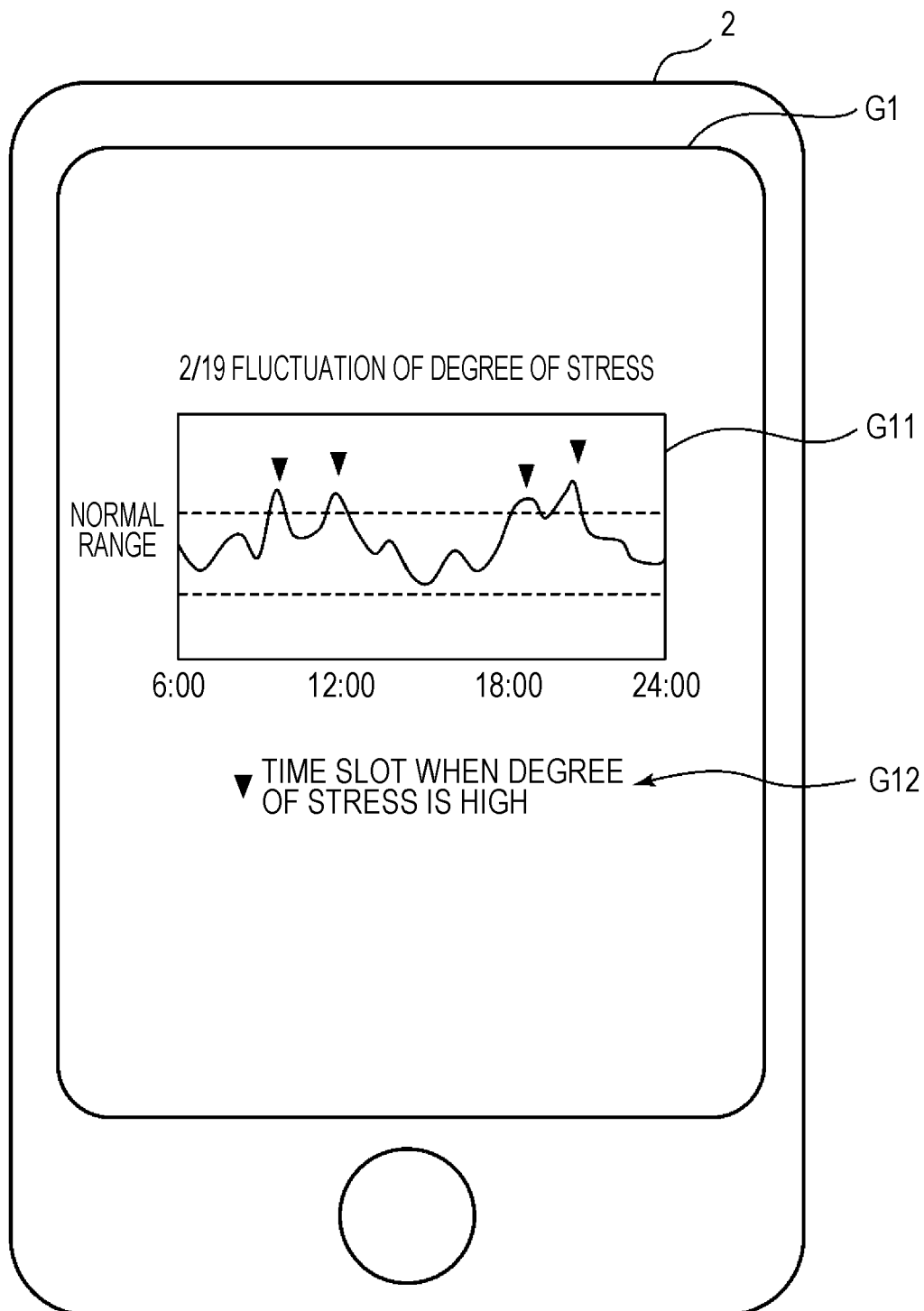
FIG. 16 is a diagram showing an example of a display screen displayed on a user terminal as time period information.

FIG. 16 is a diagram showing an example of display screen G1 displayed on user terminal 2 as time period information. Display screen G1 includes graph G11 and message display field G12.

Graph G11 shows a temporal transition of the degree of stress in the biological data obtained in the prescribed period (one day on February 19th, in this case). In graph G11, the vertical axis represents the degree of stress, and the horizontal axis represents time. The degree of stress corresponds to the biogas concentration. In graph G11, the triangular markers are displayed at the points at which the degree of stress exceeded the upper limit of the normal range. This display indicates the user the time period when the biogas concentration exceeded the upper limit of the normal range. This configuration enables the user to look back his or her life in the prescribed period and to know the reason (stressor) why the stress became high.

In message display field G12, there is displayed a message notifying the user that the triangular markers are in the time period when the degree of stress was high.

(Schedule Information)

In this embodiment, display screen G1 shown in FIG. 16 may display schedule information of the concerning user. In this case, server 1 may include a data base that manages the schedule information of the user.

The data base managing the schedule information stores, for example, pieces of information such as "user ID", "schedule", and "date and time" in association with each other. "Schedule" is a schedule of the user (for example, "conference" and the like), and is input by the user via, for example, user terminal 2. "Date and time" is a scheduled date and time when the schedule written in "schedule" is to be done and is input by the user via user terminal 2.

When transmitting the time period information, server 1 transmits to user terminal 2 the schedule information of the concerning user in the prescribed period by embedding the schedule information in the time period information.

User terminal 2 may generate display screen G1 by using the schedule information. As a display form of the schedule information, an aspect can be employed in which the schedule information is displayed in graph G11 in association with the time period of the user. For example, a form may be employed in which the schedule of the user is displayed in association with the time shown on graph G11. This display enables the user to easily check the causation between stress and behaviors of the user herself.

As described above, the first embodiment makes it possible to objectively determine a stress amount by using tetradecane, which is biogas that is supposed to have a relationship with stress. Therefore, it is possible to objectively grasp a degree of accumulation of stress without being affected by a subjective feeling of a person.

Further, in the first embodiment, by displaying, on user terminal 2, the time period when the upper limit of the normal range is exceeded, the user can, for example, look back on a day and objectively grasp how much stress the user felt on the day. Further, in the first embodiment, by taking as a clue what happened to the user in the time period when the upper limit of the normal range was exceeded, the user can find out the user's stressor.

Second Embodiment

Figure 17:
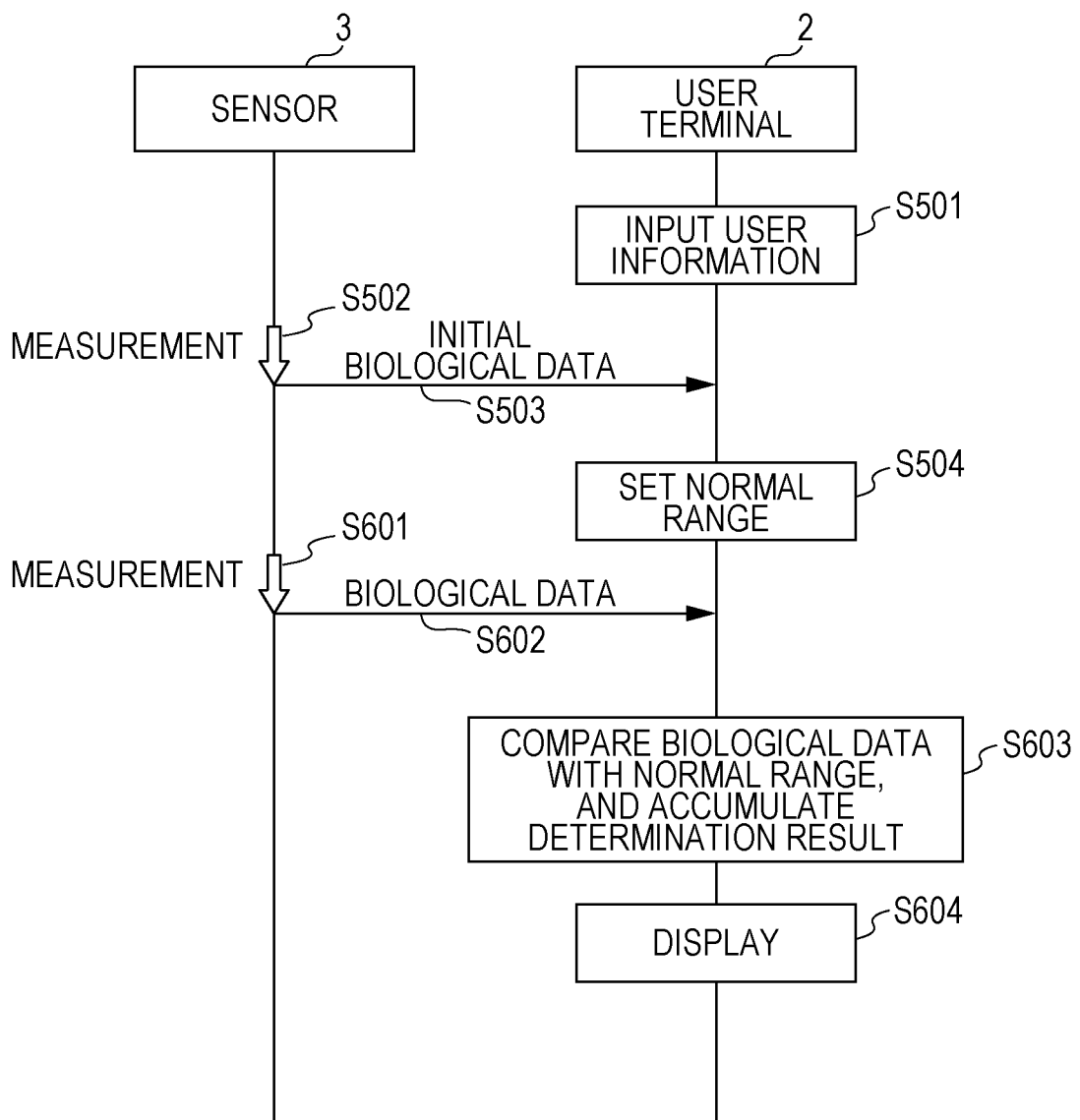
FIG. 17 is a sequence diagram showing a process in an information processing system according to a second embodiment of the present disclosure.

In the second embodiment, the functions of server 1 are incorporated in user terminal 2. Note that in the second embodiment, the same components as in the first embodiment are assigned the same reference signs and are not described again. FIG. 17 is a sequence diagram showing a process in an information processing system according to the second embodiment of the present disclosure.

In FIG. 17, the difference from FIG. 13 is that server 1 is omitted and that information processing system is configured with sensor 3 and user terminal 2. Steps S501 to S504 correspond to the initial phase.

Steps S501, S502, and S503 are the same as steps S101, S103, and S104 in FIG. 13. Step S504 is the same as step S106 in FIG. 13 except that step S504 is performed not on server 1 but on user terminal 2.

Steps S601 to S604 correspond to the normal phase. Steps S601 and S602 are the same as steps S201 and S202 in FIG. 13. Step S603 is the same as step S204 in FIG. 13 except that step S603 is performed not on server 1 but on user terminal 2.

In step S604, if the determination result of step S603 indicates abnormal, controller 21 of user terminal 2 causes display unit 23 to display information indicating that the stress of the user is out of the normal range. On the other hand, in step S604, if the determination result of step S603 indicates normal, controller 21 of user terminal 2 causes display unit 23 to display information indicating that the stress of the user is within the normal range.

Figure 18:
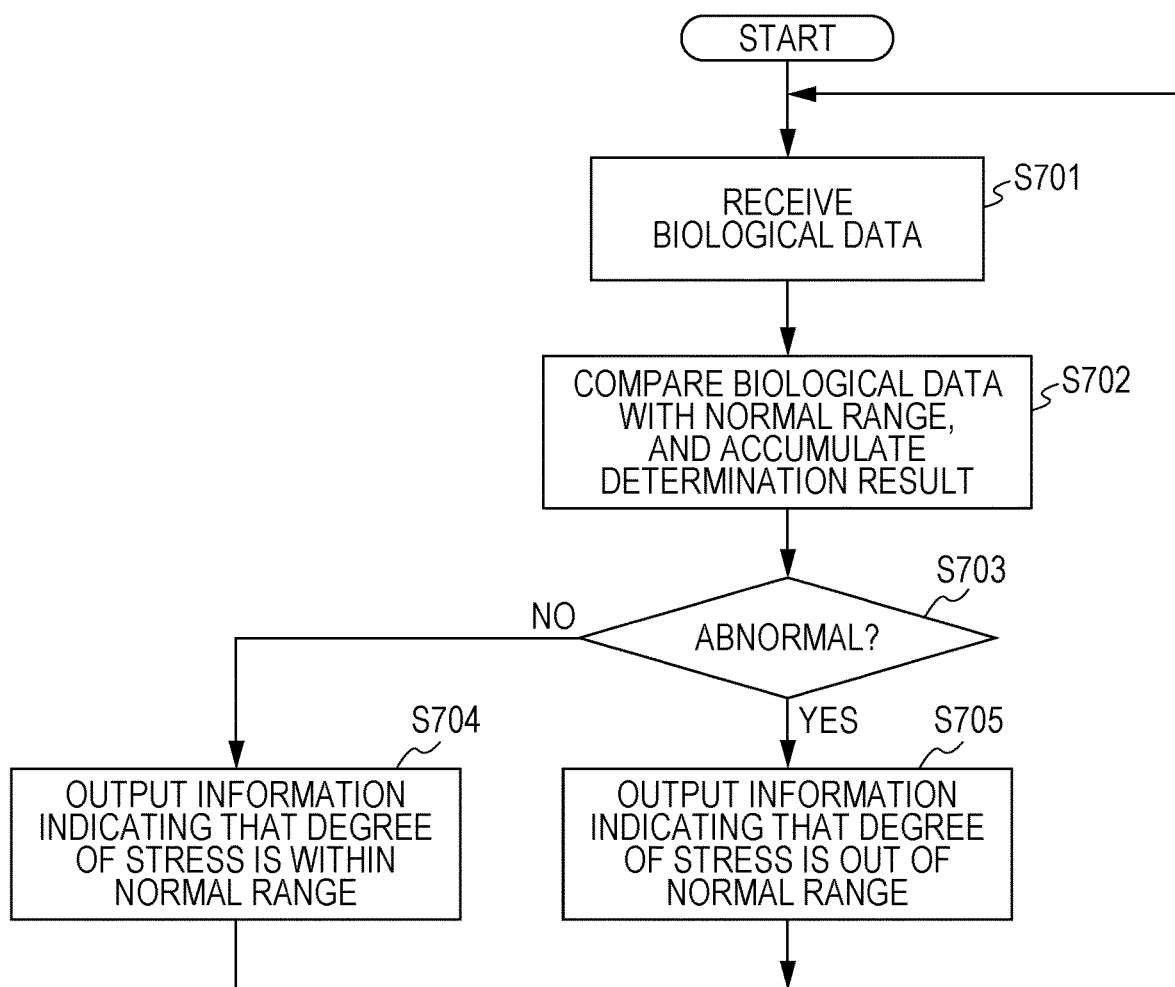
FIG. 18 is a flowchart showing details of a process of a normal phase according to the second embodiment of the present disclosure.

Note that in the second embodiment, a flowchart of the initial phase is the same as the flowchart of FIG. 14. FIG. 18 is a flowchart showing details of the process of the normal phase according to the second embodiment of the present disclosure. Note that the flowchart is performed on user terminal 2.

First, communication unit 24 receives the biological data from sensor 3 (step S701). Next, controller 21 determines whether the stress state is normal or abnormal, by comparing the biogas concentration indicated by the biological data with the normal range for the concerning user, and controller 21 accumulates the determination result in biological data table T4 (step S702).

Next, if the determination result of step S703 indicates abnormal (step S703: YES) controller 21 causes display unit 23 to display information indicating that the degree of stress (biogas concentration) got out of the normal range (step S705). In this step, as the information indicating that the degree of stress got out of the normal range, a message saying, for example, "Stress is high" may be used.

On the other hand, the determination result of step S703 indicates not abnormal, in other words, indicates normal (step S703: NO), controller 21 causes display unit 23 to display information indicating that the degree of stress (biogas concentration) is within the normal range (S704). In this step, as the information indicating that the degree of stress is within the normal range, a message saying, for example, "Stress is normal" can be used.

If step S704 or S705 is finished, the process goes back to step S701.

As described above, in the information processing system according to the second embodiment, the information indicating whether the degree of stress is within the normal range is displayed on display unit 23; therefore, the user can be notified of an objective determination result indicating whether the user is currently in a stress state.

In the present disclosure, the following variations can be employed.

(1) In the above description, sensor 3 is integrally configured, but the present disclosure is not limited to the above configuration. FIG. 19 is a diagram showing an example of sensor 3 according to a variation of the present disclosure. Regarding sensor 3 according to the variation, wearable part 3A to be mounted on a user and main body part 3B are separately configured. Wearable part 3A is configured with a fitting belt that is detachable to the arm at a point near the underarm of the user. Wearable part 3A is attached with an absorbent for absorbing a biogas.

Wearable part 3A is configured to be detachable also to main body part 3B. Main body part 3B includes detection unit 33, controller 31, and communication unit 34 shown in FIG. 7. When wearable part 3A is attached to main body part 3B, main body part 3B heats the adsorbent with, for example, a heater to desorb the biogas from the adsorbent, analyzes the biogas, extracts a measurement object biogas (tetradecane in this embodiment), and measures a biogas concentration. Then, main body part 3B transmits the biological data including the measured biogas concentration to user terminal 2. In this variation, wearable part 3A is made compact, and a user's burden can be thus reduced.

(2) In the second embodiment, user terminal 2 may be configured with a computer used by a doctor who examines the user. In this case, at the time of examination, the doctor may make the user wear sensor 3 and cause user terminal 2 to acquire the biological data and to determine the stress of the user.

Alternatively, the doctor may cause user terminal 2 to acquire the biological data previously measured by sensor 3 for a prescribed period (for example, one, two, or three days) and to thus determine the stress of the user. In this case, the user is instructed by the doctor to wear sensor 3 beforehand. Sensor 3 stores the biological data measured in this prescribed period in memory 32 in association with the measurement time. Memory 32 is a memory detachable to sensor 3.

User brings memory 32 to the hospital when visiting the hospital. The doctor connects this memory 32 to user terminal 2 to cause user terminal 2 to acquire the biological data obtained in the prescribed period. Then, if the biogas concentration indicated by the acquired biological data exceeds the upper limit of the normal range, user terminal 2 causes display unit 23 to display information indicating the fact. On the other hand, if the biogas concentration indicated by the acquired biological data is less than or equal to the upper limit of the normal range, user terminal 2 causes display unit 23 to display information indicating the fact.

This variation can provide a doctor who makes a diagnosis of conditions of the user visiting the hospital, with data useful to prevent a mental disorder. Note that the present variation may be applied to a regular health examination.

INDUSTRIAL APPLICABILITY

The present disclosure is expected to prevent a mental disorder and is therefore useful for an information processing system that manages stress of a user.

REFERENCE SIGNS LIST 1 server
2 user terminal
3 sensor
11 controller
12 memory
13 communication unit
21 controller
22 memory
23 display unit
24 communication unit
31 controller
32 memory
33 detection unit
34 communication unit
111 data analyzer
NT network
T2 normal range data table
T4 biological data table
U1 user

The invention claimed is:

1. A method for providing information in an information processing system, the method comprising:
acquiring, via a network, biogas information at multiple timings and time information corresponding to each of the multiple timings, wherein the biogas information represents a concentration of tetradecane of a user acquired by a sensor that detects tetradecane discharged from a skin surface of the user;
obtaining reference information representing an upper limit of a normal range of the concentration of tetradecane per unit period of time, using a memory storing the reference information representing the upper limit of the normal range;
determining a stress time period during which a concentration of the tetradecane of the user is more than the upper limit of the normal range, based on the acquired biogas information; and
outputting time period information indicating the determined stress time period to an information terminal of the user, to display the stress time period indicated by the time period information on a display of the information terminal.

2. The method according to claim 1, wherein
the upper limit of the normal range of the concentration of tetradecane per the unit period of time is set for the user as individual information of the user, based on the biogas information acquired in a predetermined period of time.

3. The method according to claim 1, wherein
the upper limit of the normal range of the concentration of tetradecane per the unit period of time is used commonly to a plurality of users including the user.

4. The method according to claim 1, wherein
the stress time period indicated by the time period information is displayed in association with schedule information on the user, on the information terminal.

5. The method according to claim 1, wherein
the sensor for detecting tetradecane is built in a device to be worn on the user.

6. The method according to claim 1, wherein
the time information corresponding to each of the multiple timings is associated with each time when the sensor detects the biogas.

7. An information processing system comprising:
a server device; and
an information terminal,
wherein the server device configured to:
acquire, via a network, biogas information at multiple timings and time information corresponding to time at each of the multiple timings, wherein the biogas information represents a concentration of tetradecane of a user acquired by a sensor that detects the tetradecane discharged from a skin surface of the user;
obtain reference information representing an upper limit of a normal range of the concentration of tetradecane per unit period of time, using a memory storing the reference information representing the upper limit of the normal range;
determine a stress time period during which a concentration of the tetradecane of the user is more than the upper limit of the normal range, based on the acquired biogas information; and
output time period information indicating the determined stress time period to the information terminal, and
wherein the information terminal displays the stress time period indicated by the time period information, on a display of the information terminal.

8. An information terminal used in the information processing system according to claim 7.

9. A method for processing information using a computer, the method comprising:
acquiring, via a network, biogas information at multiple timings and time information corresponding to time at each of the multiple timings, wherein the biogas information represents a concentration of tetradecane of a user acquired by a sensor that detects tetradecane discharged from a skin surface of the user;
obtaining reference information representing an upper limit of a normal range of the concentration of tetradecane per unit period of time, using a memory storing the reference information representing the upper limit of the normal range;

determining a stress time period during which a concentration of the tetradecane of the user is more than the upper limit of the normal range, based on the acquired biogas information; and outputting notice information representing that stress on the user is more than the upper limit of a predetermined normal range within the determined stress time period to display the notice information on a display.

10. The method according to claim 9, wherein the display is provided on an information terminal of the user.

* * * * *